(12) United States Patent
Kawabata et al.

(10) Patent No.: US 10,005,780 B2
(45) Date of Patent: Jun. 26, 2018

(54) PRODUCTION METHOD OF IMIDAZOLE DERIVATIVES

(71) Applicant: Takeda Pharmaceutical Company Limited, Osaka-Shi (JP)

(72) Inventors: Yoichi Kawabata, Osaka (JP); Yasuhiro Sawai, Osaka (JP); Kazuaki Kanno, Osaka (JP); Naotaka Sawada, Osaka (JP)

(73) Assignee: Takeda Pharmaceutical Company, Osaka-shi (JP)

( * ) Notice: Subject to any disclaimer, the term of this patent is extended or adjusted under 35 U.S.C. 154(b) by 0 days. days.

(21) Appl. No.: 15/002,692

(22) Filed: Jan. 21, 2016

(65) Prior Publication Data

US 2016/0244454 A1    Aug. 25, 2016

Related U.S. Application Data

(62) Division of application No. 14/123,381, filed as application No. PCT/JP2012/065795 on Jun. 14, 2012, now Pat. No. 9,278,938.

(30) Foreign Application Priority Data

Jun. 15, 2011 (JP) .................................. 2011-133712

(51) Int. Cl.
    C07D 487/04 (2006.01)
    C07D 233/64 (2006.01)

(52) U.S. Cl.
    CPC ......... *C07D 487/04* (2013.01); *C07D 233/64* (2013.01)

(58) Field of Classification Search
    CPC .................................................. C07D 487/04
    See application file for complete search history.

(56) References Cited

U.S. PATENT DOCUMENTS

| | | |
|---|---|---|
| 6,649,643 B1 | 11/2003 | Tasaka et al. |
| 6,713,632 B1 | 3/2004 | Kawakami |
| 7,662,974 B2 | 2/2010 | Kawakami et al. |
| 2002/0013501 A1 | 1/2002 | Sorger et al. |
| 2004/0033935 A1 | 2/2004 | Tasaka et al. |
| 2004/0096211 A1* | 5/2004 | Sorger .................. C07C 67/343 396/661 |
| 2005/0043544 A1 | 2/2005 | Nuwa et al. |
| 2010/0105922 A1 | 4/2010 | Kawakami et al. |
| 2012/0077985 A1 | 3/2012 | Kawakami et al. |

FOREIGN PATENT DOCUMENTS

| | | |
|---|---|---|
| EP | 1471056 A1 | 10/2004 |
| JP | 58-032880 | 2/1983 |
| JP | 2002-047247 A | 2/2002 |
| JP | 2003-201282 A | 7/2003 |
| WO | 01/30762 A1 | 5/2001 |
| WO | 02/40484 A2 | 5/2002 |
| WO | 03/059889 A1 | 7/2003 |

OTHER PUBLICATIONS

Jikken Kagaku Kouza 5th, vol. 18, 2004, 72-75 and 79-80, the Chemical Society of Japan (partial Enlish language translation).
Partial English Language translation of JP 58-032880, published on Feb. 25, 1983.
Office Action dated May 24, 2016 in corresponding Japanese Patent Application No. 2013-549084.
M.J. Girgis et al., "A Scalable Zinc Activation Procedure Using DIBAL-H in a Reformatsky Reaction", Organic Process Research & Development vol. 13, pp. 1094-1099 (2009).
K. Kitagawa et al., "Halogen—Magnesium Exchange via Trialkylmagnesates for the Preparation of Aryl- and Alkenylmagnesium Reagents", Angew Chem. Int. Ed., 39(14), pp. 2481-2483 (2000).
Jikken Kagaku Kouza 5th, vol. 18, 2004, 72-75 and 79-80, the Chemical Society of Japan (Japanese language).
P. Knochel et al., "Highly Functionalized Organomagnesium Reagents Prepared Through Halogen-Metal Exchange", Angewandte Chemie International Edition, 42(36), pp. 4302-4320 (2003).
International Search Report dated Nov. 23, 2012 in corresponding PCT/JP2012/065795.
Bayh et al., "Deprotonation of Benzoxazole and Oxazole Using Lithium Magnesates", J. Org. Chem., vol. 70, pp. 5190-5196 (2005).
Inoue et al., "Selective Halogen-Magnesium Exchange Reaction via Organomagnesium Ate Complex", J. Org. Chem., vol. 66, pp. 4333-4339 (2001).
Kitagawa et al., Angewandte Chemie International Edition, 39(14), pp. 2481-2483 (Jul. 17, 2000).

\* cited by examiner

*Primary Examiner* — Laura L. Stockton
(74) *Attorney, Agent, or Firm* — Mintz Levin Cohn Ferris Glovsky and Popeo, P.C.; David G. Conlin; Joohee Lee

(57) ABSTRACT

The present invention provides an advantageous production method of an imidazole derivative, which is suitable for industrial production. Compound (VI) is produced by reacting compound (I) with a Grignard reagent or a magnesium reagent, and a lithium reagent, and then reacting the resulting compound with compound (V).

7 Claims, 2 Drawing Sheets

PRODUCTION METHOD OF IMIDAZOLE DERIVATIVES

CROSS REFERENCE TO RELATED APPLICATION

The present application is a divisional application of the U.S. patent application Ser. No. 14/123,381 filed Dec. 2, 2013, which was the National Phase Application of the International Patent Application No. PCT/JP2012/065795 filed Jun. 14, 2012, which also claimed the benefit of priority of the Japanese Patent No. 2011-133712 filed Jun. 15, 2011. The entire contents of those applications are incorporated herein for all purposes by this reference.

TECHNICAL FIELD

The present invention relates to an industrially advantageous production method of an imidazole derivative.

BACKGROUND OF THE INVENTION

It is known that an imidazole derivative represented by the following formula (Ia):

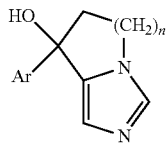

(Ia)

wherein n is an integer of 1 to 3, and Ar is an aromatic ring optionally having substituent(s), or a salt thereof has high safety and superior steroid $C_{17-20}$ lyase inhibitory activity, and is useful for the prophylaxis or treatment of diseases for which androgen or estrogen is an aggravating factor (patent document 1).

As the production method of the above-mentioned imidazole derivative, the methods described in patent document 1 and patent document 2 are known.

However, there is a demand for an advantageous production method of the imidazole derivative, which is suitable for industrial production.

DOCUMENT LIST

Patent Document

Patent Document 1: WO 02/40484
Patent Document 2: WO 03/059889

SUMMARY OF THE INVENTION

Problems to be Solved by the Invention

In the production method of patent document 2, the synthetic reaction of the following formula (Ib):

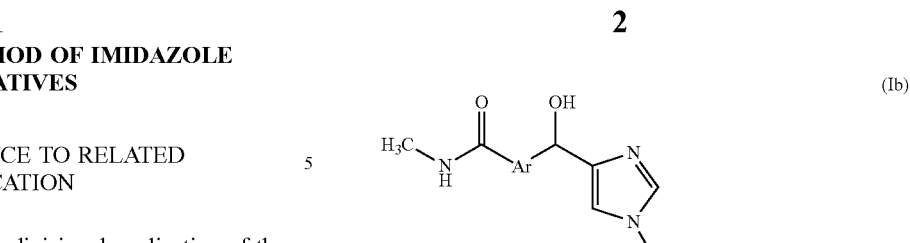

(Ib)

wherein Ar is an aromatic hydrocarbon group optionally having substituent(s), and PG is an imidazole-protecting group, which is an intermediate for synthesizing the above-mentioned formula (Ia), needs to be carried out in the presence of an organic lithium compound at an ultralow temperature of −65° C.

In view of such situation, an object of the present invention is to provide a novel production method of an imidazole derivative represented by the above-mentioned formula (Ia), particularly 6-(7-hydroxy-6,7-dihydro-5H-pyrrolo[1,2-c]imidazol-7-yl)-N-methyl-2-napht-hamide or a salt thereof, which is suitable for efficient and convenient industrial production. In addition, another object of the present invention is to provide a production method of a compound useful as an intermediate for synthesizing 6-(7-hydroxy-6,7-dihydro-5H-pyrrolo[1,2-c]imidazol-7-yl)-N-methyl-2-napht-hamide or a salt thereof, specifically the below-mentioned compound (VI) and compound (IX), which is suitable for efficient and convenient industrial production.

Means of Solving the Problems

The present inventors have conducted intensive studies in an attempt to solve the above-mentioned problems and found that the synthetic reaction of a compound represented by the above-mentioned formula (Ib), particularly the below-mentioned compound (VI), can proceed under mild conditions by using an organic magnesium compound together with an organic lithium compound, which resulted in the completion of the present invention.

Accordingly, the present invention is as follows; [1] A method of producing a compound represented by the formula:

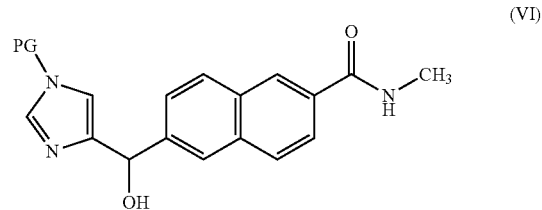

(VI)

wherein PG is a protecting group,
or a salt thereof (hereinafter sometimes to be referred to as compound (VI)), which comprises Step (1): a step of reacting a compound represented by the formula:

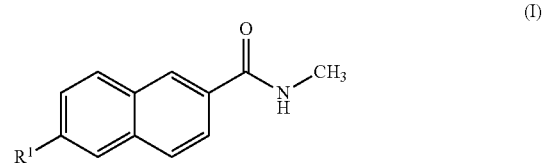

(I)

wherein R¹ is an iodine atom or a bromine atom,
(hereinafter sometimes to be referred to as compound (I))
with a compound represented by the formula:

  (II)

wherein R² is a $C_{1-6}$ alkyl group or a $C_{6-12}$ aryl group; and
X is a chlorine atom, a bromine atom or an iodine atom,
(hereinafter sometimes to be referred to as compound (II)), or a compound represented by the formula:

  (III)

wherein R²' is a $C_{1-6}$ alkyl group or a $C_{6-12}$ aryl group; and
R² is as defined above,
(hereinafter sometimes to be referred to as compound (III)), and a compound represented by the formula:

  (IV)

wherein R³ is a $C_{1-6}$ alkyl group or a $C_{6-12}$ aryl group,
(hereinafter sometimes to be referred to as compound (IV)), and then reacting the resulting compound with a compound represented by the formula:

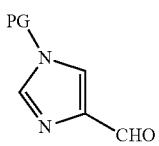  (V)

wherein PG is as defined above,
or a salt thereof (hereinafter sometimes to be referred to as compound (V)).

[2] A method of producing 6-(7-hydroxy-6,7-dihydro-5H-pyrrolo[1,2-c]imidazol-7-yl)-N-methyl-2-napht-hamide or a salt thereof, which comprises
Step (1): a step of reacting a compound represented by the formula:

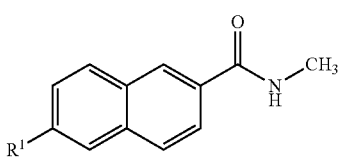  (I)

wherein R¹ is an iodine atom or a bromine atom, with a compound represented by the formula:

  (II)

wherein R² is a $C_{1-6}$ alkyl group or a $C_{6-12}$ aryl group; and
X is a chlorine atom, a bromine atom or an iodine atom,
or a compound represented by the formula:

  (III)

wherein R²' is a $C_{1-6}$ alkyl group or a $C_{6-12}$ aryl group; and
R² is as defined above, and a compound represented by
the formula:

  (IV)

wherein R³ is a $C_{1-6}$ alkyl group or a $C_{6-12}$ aryl group, and
then reacting the resulting compound with a compound represented by the formula:

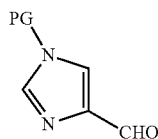  (V)

wherein PG is a protecting group,
or a salt thereof;
Step (2): a step of subjecting a compound represented by the formula:

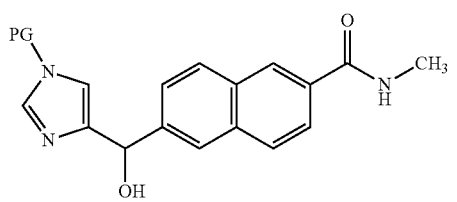  (VI)

wherein PG is as defined above,
or a salt thereof, (hereinafter sometimes referred to as compound (VI)), which is obtained in Step (1), to oxidation; Step (3): a step of reacting a compound represented by the formula:

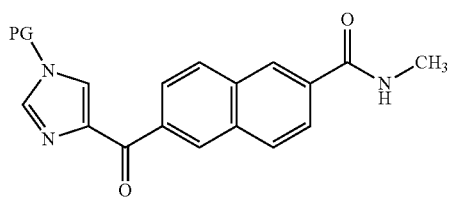  (VII)

wherein PG is as defined above,
or a salt thereof (hereinafter sometimes to be referred to as compound (VII)), which is obtained in Step (2), with a compound represented by the formula:

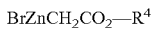  (VIII)

wherein R⁴ is a $C_{1-6}$ alkyl group,
(hereinafter sometimes to be referred to as compound (VIII)); Step (4): a step of subjecting a compound represented by the formula:

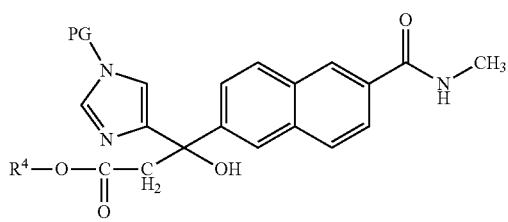  (IX)

wherein each symbol is as defined above,
or a salt thereof (hereinafter sometimes to be referred to as compound (IX)), which is obtained in Step (3), to reduction; and Step (5): a step of subjecting a compound represented by the formula:

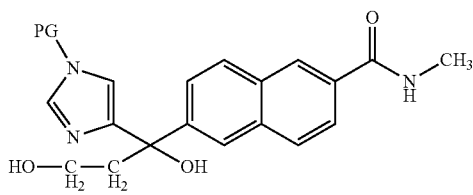

wherein PG is as defined above, or a salt thereof (hereinafter sometimes to be referred to as compound (X)), which is obtained in Step (4), to cyclization and deprotection.

[3] A method of producing of a compound represented by the formula:

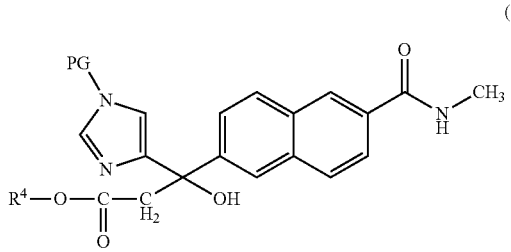

wherein PG is a protecting group; and $R^4$ is a $C_{1-6}$ alkyl group, or a salt thereof, which comprises Step (3a): a step of reacting a compound represented by the formula:

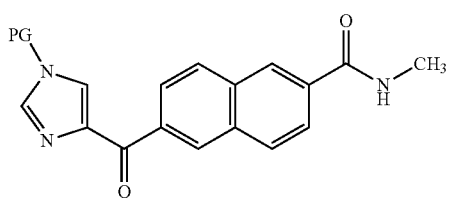

wherein PG is as defined above, or a salt thereof, with a compound represented by the formula:

  (VIII)

wherein $R^4$ is as defined above, and then adding citric acid to the obtained reaction mixture.

[4] A method of producing of 6-(7-hydroxy-6,7-dihydro-5H-pyrrolo[1,2-c]imidazol-7-yl)-N-methyl-2-napht-hamide or a salt thereof, which comprises Step (3a): a step of reacting a compound represented by the formula:

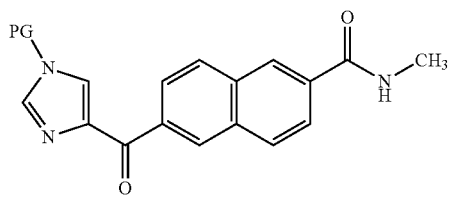

wherein PG is a protecting group, or a salt thereof, with a compound represented by the formula

  (VIII)

wherein $R^4$ is a $C_{1-6}$ alkyl group, and then adding citric acid to the obtained reaction mixture;

Step (4): a step of subjecting a compound represented by the formula:

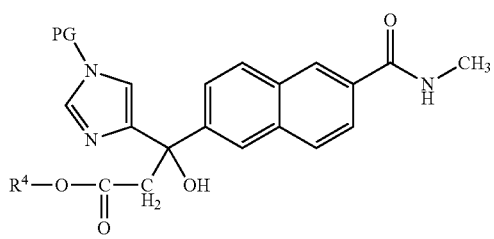

wherein each symbol is as defined above, or a salt thereof, which is obtained in Step (3a), to reduction; and Step (5): a step of subjecting a compound represented by the formula:

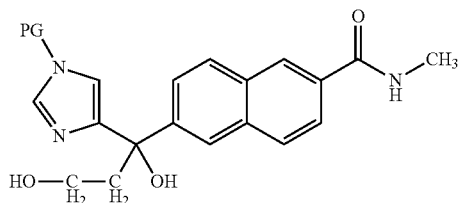

wherein PG is as defined above, or a salt thereof, which is obtained in Step (4), to cyclization and deprotection.

[5] The method of any of the above-mentioned [1] to [4], wherein PG is trityl.

[6] The method of any of the above-mentioned [1] to [4], wherein PG is tosyl, benzenesulfonyl or N,N-dimethylaminosulfonyl.

[7] The method of the above-mentioned [2], wherein Step (3) is Step (3a): a step of reacting a compound represented by the formula:

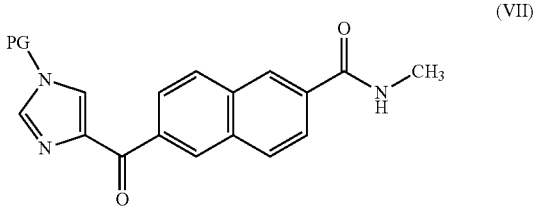
(VII)

wherein PG is a protecting group,
or a salt thereof, with a compound represented by the formula:

    (VIII)

wherein $R^4$ is a $C_{1-6}$ alkyl group,
and then adding citric acid to the obtained reaction mixture.

Effect of the Invention

The production method of the present invention using, as organic metal reagents, an organic lithium compound and an organic magnesium compound, for the production of compound (VI) does not require the reaction to be carried out at an ultralow temperature (for example, −65° C.)

In addition, work-up of the reaction mixture by adding citric acid after completion of the reaction in the production of compound (IX) suppresses decomposition of compound (IX) as well as the amount of the zinc remaining in the reaction mixture. As a result, the yield and purity of compound (IX) can be improved, and the yield and purity of the final product, 6-(7-hydroxy-6,7-dihydro-5H-pyrrolo[1,2-c]imidazol-7-yl)-N-methy-1-2-naphthamide or a salt thereof, and the object product in each step up to the final product can also be improved.

Accordingly, the production method of the present invention is a method of producing 6-(7-hydroxy-6,7-dihydro-5H-pyrrolo[1,2-c]imidazol-7-yl)-N-methyl-2-napht-hamide or a salt thereof, which is suitable for efficient and convenient industrial production.

DETAILED DESCRIPTION OF THE INVENTION

Figure 1:
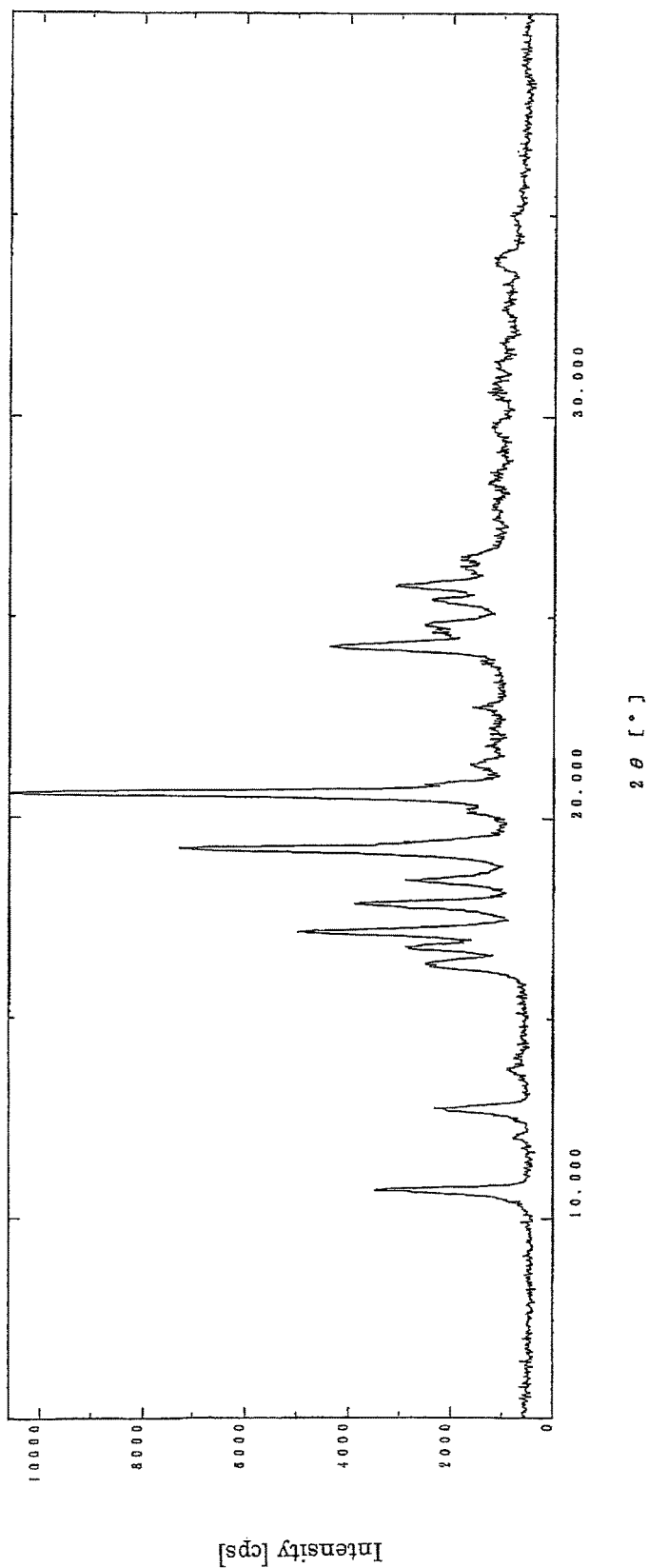
FIG. 1 shows a powder X-ray diffraction pattern of 6-((7S)-hydroxy-6,7-dihydro-5H-pyrrolo[1,2-c]imidazol-7-yl)-N-methyl-2-na-phthamide 1 hydrate.

In the present specification, the "$C_{1-6}$ alkyl group" means methyl, ethyl, n-propyl, isopropyl, n-butyl, isobutyl, sec-butyl, tert-butyl, n-pentyl, isopentyl, neopentyl, 1-ethylpropyl, n-hexyl, isohexyl, 1,1-dimethylbutyl, 2,2-dimethylbutyl, 3,3-dimethylbutyl, 2-ethylbutyl or the like, and is preferably a $C_{1-4}$ alkyl group.

In the present specification, the "$C_{1-4}$ alkyl group" means methyl, ethyl, n-propyl, isopropyl, n-butyl, isobutyl, sec-butyl, tert-butyl or the like.

In the present specification, the "$C_{6-12}$ aryl group" means phenyl, 1-naphthyl, 2-naphthyl or the like.

In the present specification, the "protecting group" means a nitrogen-protecting group (e.g., a formyl group, a $C_{1-6}$ alkyl-carbonyl group, a $C_{1-6}$ alkoxy-carbonyl group (e.g., tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethoxybenzyl), a $C_{1-6}$ alkylsulfonyl group (e.g., methanesulfonyl), a $C_{6-12}$ arylsulfonyl group (e.g., benzenesulfonyl, tosyl (toluenesulfonyl)), an N,N-di-$C_{1-6}$ alkylaminosulfonyl group (e.g., N,N-dimethylaminosulfonyl) etc.). The protecting group is optionally substituted by 1 to 3 substituents selected from a halogen atom, a $C_{1-6}$ alkoxy group and a nitro group.

$R^1$ is preferably a bromine atom.
$R^2$ is preferably a $C_{1-6}$ alkyl group, more preferably a $C_{1-4}$ alkyl group, more preferably isopropyl.
$R^{2'}$ is preferably a $C_{1-6}$ alkyl group, more preferably a $C_{1-4}$ alkyl group.
$R^3$ is preferably a $C_{1-4}$ alkyl group, more preferably butyl.
$R^4$ is preferably a $C_{1-4}$ alkyl group, more preferably ethyl.
X is preferably a chlorine atom.
PG is preferably trityl. In another embodiment, PG is preferably tosyl, benzenesulfonyl or N,N-dimethylaminosulfonyl.

Each step in the production method of the present invention is explained in the following.

[Step 1]

In Step 1, compound (VI) is obtained by reacting compound (I) with compound (II) or compound (III), and compound (IV), and then reacting the resulting compound with compound (V).

First, compound (I) is reacted with compound (II) or compound (III), and compound (IV) (Step 1a). Since the intermediate produced by the reaction has a magnesiated methylamido group, and therefore, it is stabilized, and the next reaction with compound (V) can be carried out under a mild condition.

Examples of the compound (II) include $C_{1-6}$ alkylmagnesium halides such as methylmagnesium chloride, ethylmagnesium chloride, isopropylmagnesium chloride, methylmagnesium bromide, ethylmagnesium bromide, isopropylmagnesium bromide and the like; and $C_{6-12}$ arylmagnesium halides such as phenylmagnesium chloride, phenylmagnesium bromide and the like. Among them, $C_{1-4}$ alkylmagnesium halides are preferable. The halide means chloride, bromide or iodide, preferably chloride or bromide, more preferably chloride. Compound (II) is preferably isopropylmagnesium chloride.

Examples of the compound (III) include di-$C_{1-6}$ alkylmagnesiums. Among them, di-$C_{1-4}$ alkylmagnesiums are preferable. Compound (III) is preferably dibutylmagnesium.

Examples of the compound (IV) include $C_{1-6}$ alkyllithiums such as n-butyllithium, sec-butyllithium, tert-butyllithium and the like; and $C_{6-12}$ aryllithiums. Among them, $C_{1-4}$ alkyllithiums are preferable. Compound (IV) is preferably n-butyllithium.

The amount of compound (II) or compound (III) to be used is generally about 0.1 to about 10 equivalents, preferably about 0.1 to about 3 equivalents, relative to compound (I).

The amount of compound (IV) to be used is generally about 1 to about 10 equivalents, preferably about 1 to about 3 equivalents, relative to compound (I).

To improve the yield and purity of the object product, the reaction is preferably carried out by adding (preferably adding dropwise) compound (II) or compound (III) to compound (I), and then adding (preferably adding dropwise) compound (IV) to the obtained mixture.

The reaction is generally carried out in a solvent.

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; ethers such as diethyl ether, diisopropyl ether, tert-butyl methyl ether, cyclopentyl methyl ether, tetrahydrofuran, dioxane, 1,2-dimethoxyethane, bis(2-trimethoxyethyl)ether and the like; aromatic halogenated hydrocarbons such as chlorobenzene, dichlorobenzene, benzotrifluoride and the like; and the like. These may be used alone or in a mixture of two or more kinds thereof at an appropriate ratio. Among them, the above-mentioned ethers and aliphatic hydrocarbons are preferable, and tetrahydrofuran, hexane, heptane and toluene are more preferable.

The amount of the solvent to be used is generally 1 to 100-fold, preferably 10 to 80-fold, relative to compound (I).

The reaction temperature is generally about −40° C. to about 200° C., preferably about −40° C. to about 40° C. When compound (II) or compound (III) is added to compound (I) and then compound (IV) is added to the obtained mixture, the addition of compound (II) or compound (III) is generally carried out at about −40° C. to about 200° C., preferably about −10° C. to about 40° C., and the addition of compound (IV) is generally carried out at −40° C. to about 200° C., preferably about −40° C. to about 10° C.

While the reaction time varies depending on the kinds of compound (I)-compound (IV) and the reaction temperature, it is generally about 5 min to about 48 hr, preferably about 1 hr to about 12 hr.

After completion of the reaction, the reaction product is used for the next reaction with compound (V) as the reaction mixture. Step 1a is preferably carried out under an inert condition such as a nitrogen atmosphere and the like.

Compound (I)-compound (IV), which are starting materials, can be produced according to a method known per se, for example, the method described in WO 03/059889.

Second, compound (VI) is obtained by reacting the reaction product obtained in Step 1a with compound (V) (Step 1b).

The amount of compound (V) to be used is generally about 0.1 to about 10 equivalents, preferably about 1 to about 3 equivalents, relative to compound (I).

The reaction is preferably carried out by adding (preferably adding dropwise) compound (V) to the reaction product obtained in Step 1a.

The reaction is generally carried out in a solvent. Examples of the solvent include those similar to the solvent exemplified in Step 1a.

The reaction temperature is generally about −40° C. to about 200° C., preferably about −40° C. to about 40° C.

While the reaction time varies depending on the kinds of compound (V) and the reaction temperature, it is generally about 5 min to about 48 hr, preferably about 1 hr to about 12 hr.

After completion of the reaction, the obtained compound (VI) can be used for the next reaction as the reaction mixture or as a crude product, or can also be isolated according to a conventional method from the reaction mixture, and can also be easily purified according to a conventional separation means (e.g., recrystallization, distillation, chromatography).

Compound (V) can be produced according to a method known per se.

[Step 2]

In Step 2, compound (VII) is obtained by subjecting compound (VI) to oxidation.

The oxidation is generally carried out using an oxidant in a solvent.

Examples of the oxidant include chromic acid-acetic acid, Jones reagent, anhydrous chromic acid-pyridine complex, manganese dioxide, silver carbonate-Celite, dimethyl sulfoxide-oxalyl chloride, aluminum alkoxide-ketone, tetrapropylammonium-perruthenate, ruthenium tetraoxide, hypochlorous acid-acetic acid, periodinane compounds, dimethyl sulfoxide-acetic anhydride, 2,2,6,6-tetramethylpiperidine-1-oxyradical-hypochlorous acid, benzenesulfenamide-N-halogenated succinimide, N-halogenated succinimide, bromine, sodium hydride and the like. Among them, manganese dioxide and sodium hydride are preferable, and manganese dioxide is particularly preferable.

The amount of the oxidant to be used is generally about 1 to about 30 equivalents, preferably about 1 to about 10 equivalents, relative to compound (VI).

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; esters such as ethyl acetate, n-butyl acetate and the like; ethers such as diethyl ether, diisopropyl ether, tert-butyl methyl ether, cyclopentyl methyl ether, tetrahydrofuran, dioxane, 1,2-dimethoxyethane, bis(2-trimethoxyethyl)ether and the like; aliphatic halogenated hydrocarbons such as dichloromethane, chloroform, dichloroethane, carbon tetrachloride and the like; aromatic halogenated hydrocarbons such as chlorobenzene, dichlorobenzene, benzotrifluoride and the like; ketones such as acetone, methyl ethyl ketone and the like; and aprotic polar solvents such as acetonitrile, N,N-dimethylformamide, N,N-dimethylacetamide, N-methylpyrrolidone, dimethylsulfoxide and the like. These may be used alone or in a mixture of two or more kinds thereof at an appropriate ratio. Among them, the above-mentioned aliphatic halogenated hydrocarbons, ethyl acetate, N,N-dimethylformamide and N,N-dimethylacetamide are preferable.

The amount of the solvent to be used is generally 1 to 100-fold, preferably 5 to 80-fold, relative to compound (VI).

The reaction temperature is generally about −40° C. to about 200° C., preferably about 0° C. to about 100° C.

While the reaction time varies depending on the kinds of compound (VI) and oxidant and the reaction temperature, it is generally about 5 min to about 48 hr, preferably about 1 to about 12 hr.

After completion of the reaction, the resultant product can be used for the next reaction as the reaction mixture or as a crude product, or can also be isolated according to a conventional method from the reaction mixture, and can also be easily purified according to a conventional separation means (e.g., recrystallization, distillation, chromatography).

[Step 3]

In Step 3, compound (IX) is obtained by reacting compound (VII) with compound (VIII).

Compound (VIII) is prepared from a compound represented by the formula:

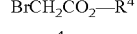

$$\text{BrCH}_2\text{CO}_2\text{—R}^4 \quad \text{(VIIIa)}$$

wherein R$^4$ is as defined above, (hereinafter sometimes to be referred to as compound (VIIIa)) and zinc.

The preparation is generally carried out by reacting compound (VIIIa) with zinc in the presence of an activator, in a solvent.

The zinc is used in the form of powder, flake, wire or foil, particularly preferably in the form of powder. Zinc may be subjected to a conventional pre-treatment by washing with an acid, or a commercially available product may be directly used.

The amount of the zinc to be used is preferably an excess amount relative to compound (VIIIa). Specifically, it is preferably 1 equivalent or more, more preferably 1 to 50 equivalents, still more preferably 1 to 5 equivalents, particularly preferably 1 to 3 equivalents, relative to compound (VIIIa).

Examples of the activator include hydroiodic acid, 1,2-dibromoethane, halogenated copper, halogenated silver, trimethylsilyl chloride and molecular sieve. Among them, trimethylsilyl chloride is preferable. In addition, zinc-copper couple, Rieke-Zn, zinc-silver-graphite, zinc chloride-lithium, zinc chloride-lithium naphthalide, zinc and zinc compound each activated by ultrasonication, and the like can be used.

The amount of the activator to be used is generally about 0.01 to about 1 equivalent, preferably about 0.01 to about 0.2 equivalent, relative to compound (VIIIa).

To improve the yield and purity of the object product, the reaction is preferably carried out by adding an activator to zinc, and then adding (preferably adding dropwise) compound (VIIIa) to the obtained mixture.

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; esters such as ethyl acetate, n-butyl acetate and the like; ethers such as diethyl ether, diisopropyl ether, tert-butyl methyl ether, tetrahydrofuran, dioxane, cyclopentyl methyl ether, 1,2-dimethoxyethane, bis(2-methoxyethyl)ether and the like; aliphatic halogenated hydrocarbons such as methylene chloride, chloroform, dichloroethane, carbon tetrachloride and the like; aromatic halogenated hydrocarbons such as chlorobenzene, dichlorobenzene, benzotrifluoride and the like; and aprotic polar solvents such as acetonitrile, N,N-dimethylformamide, N,N-dimethylacetamide, N-methylpyrrolidone, dimethylsulfoxide and the like. These may be used alone or in a mixture of two or more kinds thereof at an appropriate ratio. Among them, the above-mentioned aliphatic hydrocarbons, aromatic hydrocarbons and ethers are preferable, and cyclopentyl methyl ether and tetrahydrofuran are more preferable. A smaller amount of water is preferably contained in the solvent, and the amount is particularly preferably 0.005% or less. When an ether such as tetrahydrofuran and the like is used as a solvent, a stabilizer (e.g., 2,6-di-t-butyl-4-methylphenol etc.) may be added thereto if desired.

The amount of the solvent to be used is generally 1 to 100-fold, preferably 5 to 30-fold, relative to compound (VIIIa).

The addition of the activator is generally carried out at about −40° C. to about 100° C., preferably 0° C. to about 60° C. While the reaction time varies depending on the kinds of the activator and the reaction temperature, it is generally about 5 min to about 10 hr, preferably about 5 min to about 2 hr.

The addition of compound (VIIIa) is generally carried out at about −40° C. to about 100° C., preferably about 0° C. to about 60° C. While the reaction time varies depending on the kinds of compound (VIIIa) and the reaction temperature, it is generally about 5 min to about 10 hr, preferably about 5 min to about 2 hr.

Compound (VIIIa) can be produced according to a method known per se.

Compound (VIII) thus prepared is used for the next reaction with compound (VII) as the reaction mixture.

The amount of compound (VIII) to be used is generally about 1 to about 10 equivalents, preferably about 1 to about 5 equivalents, relative to compound (VII).

In addition, an amine may be added to compound (VIII) in order to promote the reaction. Examples of the amine include aromatic amines such as pyridine, lutidine, quinoline, bipyridyl and the like; and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, N,N'-tetramethylethylenediamine and the like.

The amount of the amine to be used is generally about 1 to about 20 equivalents, preferably about 1 to about 10 equivalents, relative to compound (VII).

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; esters such as ethyl acetate, butyl acetate and the like; ethers such as diethyl ether, diisopropyl ether, tert-butyl methyl ether, tetrahydrofuran, dioxane, cyclopentyl methyl ether, 1,2-dimethoxyethane, bis(2-methoxyethyl)ether and the like; aliphatic halogenated hydrocarbons such as methylene chloride, chloroform, dichloroethane, carbon tetrachloride and the like; aromatic halogenated hydrocarbons such as chlorobenzene, dichlorobenzene, benzotrifluoride and the like; and aprotic polar solvents such as acetonitrile, N,N-dimethylformamide, N,N-dimethylacetamide, N-methylpyrrolidone, dimethylsulfoxide and the like. These may be used alone or in a mixture of two or more kinds thereof at an appropriate ratio. Among them, the above-mentioned aliphatic hydrocarbons, aromatic hydrocarbons and ethers are preferable, and cyclopentyl methyl ether and tetrahydrofuran are more preferable.

The reaction temperature is generally about −80° C. to about 150° C., preferably −40° C. to about 20° C.

While the reaction time varies depending on the kinds of compound (VII) and compound (VIII) and the reaction temperature, it is generally about 5 min to about 20 hr, preferably about 30 min to about 5 hr.

After completion of the reaction, an acid is preferably added to the reaction mixture. The zinc which has been mixed up with compound (VIII) (the zinc which is remaining in the reaction mixture of compound (VIII)) can be removed by the addition of the acid to the reaction mixture. In addition, compound (IX) can be obtained in high yield by the addition of the acid to the reaction mixture.

Examples of the acid include inorganic acids such as hydrochloric acid, hydrobromic acid, nitric acid, sulfuric acid, phosphoric acid and the like; and organic acids such as formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Among them, citric acid, tartaric acid, succinic acid, malic acid, fumaric acid and maleic acid are preferable, and citric acid is particularly preferable, since the zinc which has been mixed up with compound (VIII) can be efficiently removed and decomposition of the reaction product, compound (IX), can be prevented.

The amount of the acid to be used is generally about 1 to about 100-fold, preferably about 5 to about 20-fold, relative to compound (VIII).

After the addition of the acid, the obtained compound (IX) can be used for the next reaction as the reaction mixture or as a crude product, or can also be isolated according to a conventional method from the reaction mixture, and can also be easily purified according to a conventional separation means (e.g., recrystallization, distillation, chromatography).

The optically active compound (IX) can be obtained by reacting compound (VII) with compound (VIII) in the presence of an asymmetric ligand.

Examples of the asymmetric ligand include optically active aminoalcohol derivatives, optically active alcohol derivatives and optically active amine derivatives. Examples of the optically active aminoalcohol derivative include cinchona alkaloids such as cinchonine, cinchonidine, quinidine, kinin and the like; N-methylephedrine, norephedrine, 3-oxo-(dimethylamino)isoborneol, 1-methyl-2-pyrrolidinemethanol, 1-benzyl-2-pyrrolidinemethanol, 2-[hydroxy(diphenyl)methyl]-1-methylpyrrolidine and 2,2'-{benzene-1,3-diylbis[methanediyl(methylimino)]}bis(1-phenylpropan-1-ol). Examples of the optically active alcohol derivative include 1,2-binaphthol. Examples of the optically active amine derivative include strychnine and sparteine. Compound (IX) having a desired steric configuration can be obtained depending on the selection of the asymmetric ligand.

The amount of the asymmetric ligand to be used is generally about 0.01 to about 5 equivalents, preferably about 0.01 to about 2 equivalents, relative to compound (VII).

Step 3 can also be performed using compound (VIII) wherein the bromine atom is replaced by an iodine atom, instead of compound (VIII).

[Step 4]

In Step 4, compound (X) is obtained by subjecting compound (IX) to reduction.

The reaction is generally carried out in the presence of a metal hydride complex compound, in a solvent. A metal halide may be added for this reaction.

Examples of the metal hydride complex compound include alkali metal hydride complex compounds such as sodium borohydride, lithium borohydride, potassium borohydride, sodium cyanoborohydride and the like; and zinc borohydride. Among them, alkali metal hydride complex compounds such as sodium borohydride, lithium borohydride, potassium borohydride and the like are preferable, sodium borohydride and potassium borohydride are more preferable, and sodium borohydride is particularly preferable.

The amount of the metal hydride complex compound to be used is generally 1 to 50 mol, preferably 2 to 10 mol, per 1 mol of compound (IX).

Examples of the metal halide include halogenated aluminums such as aluminum chloride, aluminum bromide and the like; halogenated lithiums such as lithium iodide, lithium chloride, lithium bromide and the like; halogenated magnesiums such as magnesium chloride, magnesium bromide and the like; halogenated calciums such as calcium chloride, calcium bromide and the like; halogenated zincs such as zinc chloride, zinc bromide and the like; iron chloride, tin chloride and boron fluoride. Among them, halogenated calciums such as calcium chloride, calcium bromide and the like; and halogenated zincs such as zinc chloride, zinc bromide and the like are preferable, halogenated calciums such as calcium chloride, calcium bromide and the like are more preferable, and calcium chloride is particularly preferable.

The amount of the metal halide to be used is generally 0.1 to 10 mol, preferably 0.1 to 5 mol, per 1 mol of compound (IX).

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; ethers such as diethyl ether, diisopropyl ether, tert-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane, carbon tetrachloride and the like; aromatic halogenated hydrocarbons such as chlorobenzene, dichlorobenzene, benzotrifluoride and the like; alcohols such as methanol, ethanol, 1-propanol, 2-propanol, 1-butanol, 2-butanol, 2-methyl-1-propanol and the like; and aprotic polar solvents such as acetonitrile, N,N-dimethylformamide, N,N-dimethylacetamide, N-methylpyrrolidone, dimethylsulfoxide and the like. These may be used alone or in a mixture of two or more kinds thereof at an appropriate ratio. Among them, the above-mentioned ethers and alcohols are preferable, mixed solvents of ethers-alcohols are more preferable, and a mixed solvent of tetrahydrofuran-ethanol, and a mixed solvent of tetrahydrofuran-methanol are particularly preferable.

The amount of the solvent to be used is 1 to 50-fold, preferably 10 to 30-fold, relative to compound (IX).

The reaction temperature is generally about −80° C. to about 200° C., preferably about −40° C. to about 40° C.

While the reaction time varies depending on the kinds of compound (IX), the metal hydride complex compound and metal halide and the reaction temperature, it is generally about 5 min to about 48 hr, preferably about 3 to about 24 hr.

After completion of the reaction, the obtained compound (X) can be used for the next reaction as the reaction mixture or as a crude product, or can also be isolated according to a conventional method from the reaction mixture, and can also be easily purified according to a conventional separation means (e.g., recrystallization, distillation, chromatography).

[Step 5]

In Step 5,6-(7-hydroxy-6,7-dihydro-5H-pyrrolo[1,2-c]imidazol-7-yl)-N-methyl-2-nap-hthamide or a salt thereof is obtained by subjecting compound (X) to cyclization and deprotection.

This reaction is generally carried out in a solvent, by (i) reacting compound (X) with an agent for conversion of hydroxyl to a leaving group, and (ii) reacting the resulting compound with a base (cyclization and deprotection).

The reactions of the above-mentioned (i) and (ii) may be carried out simultaneously or stepwisely in no particular order.

Examples of the agent for conversion of hydroxyl to a leaving group include halogenated sulfonyls such as methanesulfonyl chloride, p-toluenesulfonyl chloride and the like; and halogenating agents such as carbon tetrachloride-triphenylphosphine, N-chlorosuccinimide-triphenylphosphine, thionyl chloride, lithium chloride, carbon tetrabromide-triphenylphosphine, N-bromosuccinimide-triphenylphosphine, phosphorus tribromide, phosphorus bromide, sodium bromide, sodium iodide, imidazole-iodine-triphenylphosphine and the like. Among them, halogenated sulfonyls such as methanesulfonyl chloride, p-toluenesulfonyl chloride and the like are preferable, and methanesulfonyl chloride is particularly preferable.

The amount of the agent for conversion of hydroxyl to a leaving group to be used is generally 1 to 10 equivalents, preferably 1 to 5 equivalents, particularly preferably 1 to 2 equivalents, relative to compound (X).

Examples of the base include organic bases and inorganic bases. Examples of the organic base include tertiary amines such as triethylamine, diisopropylethylamine, tri(n-propyl) amine, tri(n-butyl)amine, cyclohexyldimethylamine, N-methylpiperidine, N-methylpyrrolidine, N-methylmorpholine and the like; and aromatic amines such as pyridine, lutidine, N,N-dimethylaniline and the like. Among them, tertiary amines such as triethylamine, diisopropylethylamine and the like are preferable. Examples of the inorganic base include hydroxides of alkali metal or alkaline earth metal such as sodium hydroxide, potassium hydroxide, lithium hydroxide, calcium hydroxide, barium hydroxide and the like; carbonates of alkali metal or alkaline earth metal such as sodium carbonate, potassium carbonate, cesium carbonate, sodium hydrogen carbonate, potassium hydrogen carbonate and the like; and phosphates such as disodium monohydrogenphosphate, dipotassium monohydrogenphosphate, trisodium phosphate, tripotassium phosphate and the like. Among them, sodium carbonate and potassium hydrogen carbonate are preferable.

The amount of the base to be used is generally 0.1 to 10 equivalents, particularly preferably 1 to 2 equivalents, relative to compound (X). The base to be used may be alone or in combination of two or more. For example, when the base is used in combination of two or more, an amine may be added in the reaction of compound (X) with an agent for conversion of hydroxyl to a leaving group, and an inorganic base may be added in the reaction (cyclization and deprotection) of the resultant product by the above-mentioned reaction with the base presented in the reaction mixture.

The solvent is not particularly limited as long as it does not adversely influence the reaction, and examples thereof include aromatic hydrocarbons such as benzene, toluene, xylene and the like; aliphatic hydrocarbons such as hexane, pentane, heptane and the like; ethers such as diethyl ether, diisopropyl ether, tert-butyl methyl ether, cyclopentyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane, carbon tetrachloride and the like; aromatic halogenated hydrocarbons such as chlorobenzene, dichlorobenzene, benzotrifluoride and the like; alcohols such as methanol, ethanol, 1-propanol, 2-propanol, 1-butanol, 2-butanol, 2-methyl-1-propanol and the like; aprotic polar solvents such as acetonitrile, N,N-dimethylformamide, N,N-dimethylacetamide, N-methylpyrrolidone, dimethylsulfoxide and the like; and water. These may be used alone or in a mixture of two or more kinds thereof at an appropriate ratio. Among them, the above-mentioned aromatic hydrocarbons, ethers, aprotic polar solvents and water are preferable, toluene, tetrahydrofuran, acetonitrile and water are more preferable, tetrahydrofuran, methanol, acetonitrile and water are still more preferable, and a mixed solvent of tetrahydrofuran-water is particularly preferable.

The amount of the solvent to be used is 1 to 50-fold, preferably 5 to 30-fold, relative to compound (X).

After completion of the reaction, the obtained 6-(7-hydroxy-6,7-dihydro-5H-pyrrolo[1,2-c]imidazol-7-yl)-N-methyl-2-napht-hamide can be isolated according to a conventional method from the reaction mixture, and can also be easily purified according to a conventional separation means (e.g., recrystallization, distillation, chromatography). For example, the purification is performed by dissolving the crude product in water-methanol, and adding dropwise water to the obtained solution under cooling.

In the present specification, 6-(7-hydroxy-6,7-dihydro-5H-pyrrolo[1,2-c]imidazol-7-yl)-N-methyl-2-napht-hamide encompasses 6-((7S)-hydroxy-6,7-dihydro-5H-pyrrolo[1,2-c]imidazol-7-yl)-N-methyl-2-na-phthamide and 6-((7R)-hydroxy-6,7-dihydro-5H-pyrrolo[1,2-c]imidazol-7-yl)-N-methyl-2-naphthamide.

6-(7-Hydroxy-6,7-dihydro-5H-pyrrolo[1,2-c]imidazol-7-yl)-N-methyl-2-naphthamide may be in the form of a salt, preferably a pharmacologically acceptable salt. Examples of the salt include salts with an inorganic base, salts with an organic base, salts with an inorganic acid, salts with an organic acid, and salts with a basic or acidic amino acid.

Preferable examples of the salts with an inorganic base include alkali metal salts such as sodium salt, potassium salt and the like; alkaline earth metal salts such as calcium salt, magnesium salt and the like; an aluminum salt; and an ammonium salt.

Preferable examples of the salts with an organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine or N,N-dibenzylethylenediamine.

Preferable examples of the salts with an inorganic acid include salts with hydrochloric acid, hydrobromic acid, nitric acid, sulfuric acid or phosphoric acid.

Preferable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferable examples of the salts with a basic amino acid include salts with arginine, lysine or ornithine.

Preferable examples of the salts with an acidic amino acid include salts with aspartic acid or glutamic acid.

In the present specification, 6-(7-hydroxy-6,7-dihydro-5H-pyrrolo[1,2-c]imidazol-7-yl)-N-methyl-2-naphthamide may be in the form of a hydrate or non-hydrate. These are encompassed in 6-(7-hydroxy-6,7-dihydro-5H-pyrrolo[1,2-c]imidazol-7-yl)-N-methyl-2-naphthamide.

Compound (V), compound (VI), compound (VII), compound (IX) and compound (X) may be in the form of a salt, and examples thereof include those similar to the salts of 6-(7-hydroxy-6,7-dihydro-5H-pyrrolo[1,2-c]imidazol-7-yl)-N-methyl-2-naphthamide.

6-(7-Hydroxy-6,7-dihydro-5H-pyrrolo[1,2-c]imidazol-7-yl)-N-methyl-2-naphthamide or a salt thereof obtained according the production method of the present invention can be used as an agent for the prophylaxis or treatment of androgen-independent prostate cancer and the like, according the method described in WO 2009/057795 and the like.

EXAMPLES

The present invention is explained in detail in the following by referring to Reference Examples and Examples, which are not to be construed as limitative.

In Reference Examples and Examples, the room temperature means about 25° C.

Reference Example 1

To 4-formylimidazole (30.0 g, 0.30 mol) were added toluene (300 mL) and triethylamine (35.0 g, 0.34 mol), and then N,N-dimethylaminosulfonyl chloride (50.0 g, 0.34 mol) was added thereto at room temperature. The mixture was stirred at 70° C. for 20 hr, and the insoluble material was collected by filtration, and washed with toluene (300 mL) to give wet crystals. To the obtained wet crystals were added water (100 mL) and ethyl acetate (300 mL), and the crystals were dissolved with stirring at room temperature. The organic layer and the aqueous layer were separated. The obtained aqueous layer was extracted with ethyl acetate (200 mL), and the organic layer and the aqueous layer were separated. The obtained organic layer and the previously obtained organic layer were combined. These operations were repeated twice, and the organic layer was completely concentrated under reduced pressure to give crude crystals (32.0 g). To the crude crystals was added ethyl acetate (90 mL), and crystals were dissolved with heating to about 60° C. The solution was slowly cooled to 30° C. for recrystallization, hexane (180 mL) was added thereto, and the mixture was stirred at room temperature for 2 hr to give crystals. The obtained crystals were collected by filtration, and washed with a mixed solvent (45 mL) of ethyl acetate/hexane (1:2, volume ratio). The obtained wet crystals were dried under reduced pressure to give 1-N,N-dimethylaminosulfonyl-4-formyl-1H-imidazole (29.4 g, 0.14 mmol). yield 48%

$^1$H NMR (500 MHz, DMSO-d$_6$) δ 2.93 (s, 6H), 7.90 (d, J=1.3 Hz, 1H), 7.96 (d, J=1.3 Hz, 1H), 9.95 (s, 1H)); HRMS (ESI) m/z Calcd for a C$_6$H$_{10}$N$_3$O$_3$S[m+H]$^+$: 204.0365. Found: 204.0438.

Reference Example 2

4-Formylimidazole (20.0 g, 208.14 mmol) and p-toluenesulfonyl chloride (43.7 g, 229.0 mmol) were suspended in N,N-dimethylacetamide (200 mL). To the obtained suspension was added dropwise triethylamine (23.2 g, 229.0 mmol) at 10° C. or below, and the mixture was stirred at 10° C. or below for 1 hr or more. To the reaction mixture was added n-heptane (60 mL) at 30° C. or below. To the obtained solution was added dropwise water (240 mL) at 30° C. or below for crystallization. The mixture was stirred at room temperature for 1 hr or more to give crystals. The obtained crystals were collected by filtration, and washed with water (300 mL) to give wet crystals. The obtained wet crystals were dried under reduced pressure at an outside temperature of 50° C. to give 1-tosyl-4-formyl-1H-imidazole (44.2 g, 176.6 mmol). yield 85%. $^1$H NMR (500 MHz, DMSO-d$_6$) δ 2.42 (s, 1H), 7.54-7.56 (m, 2H), 8.06-8.08 (m, 2H), 8.58 (s, 1H), 8.66 (s, 1H), 9.76 (s, 1H).

Reference Example 3

4-Formylimidazole (11.7 g, 121.8 mmol) and acetonitrile (59 mL) were charged, and triethylamine (13.6 g, 133.9 mml) was added thereto at 30° C. or below. And then, a solution of benzenesulfonyl chloride (23.7 g, 133.9 mmol) in THF (35 mL) was added dropwise thereto at 30° C. or below, and the mixture was stirred at room temperature for 1 hr or more. After the reaction, water (94 mL) was added dropwise thereto at 30° C. or below for crystallization, and the mixture was stirred at room temperature for 1 hr or more, cooled to 10° C. or below, and stirred for 1 hr or more. The obtained crystals were collected by filtration, and washed with a mixed solvent (35 mL) of acetonitrile/water (1:2, volume ratio). The obtained wet crystals were dried under reduced pressure at an outside temperature of 50° C. to give 1-(phenylsulfonyl)-4-formyl-1H-imidazole (20.0 g, 84.7 mmol). yield 70%.

$^1$H NMR (500 MHz, DMSO-d$_6$) δ 7.74-7.77 (m, 2H), 7.88-7.89 (m, 1H), 8.19-8.21 (m, 2H), 8.62 (s, 1H), 8.70 (d, J=5.0 Hz, 1H), 9.76 (s, 1H); HRMS (ESI) m/z Calcd for a C$_{10}$H$_9$N$_2$O$_3$S[M+H]$^+$: 237.0289. Found: 237.0330.

Reference Example 4

To a solution of 4-formylimidazole (10.0 g, 104.1 mmol) in tetrahydrofuran (100 mL) were added triethylamine (12.6 g, 124.9 mmol) and a catalytic amount of 4-dimethylaminopyridine (2.5 g, 20.8 mmol). A solution of di-t-butyl-dicarbonate (27.3 g, 124.9 mmol) in THF (50 mL) was added dropwise thereto at 30° C. or below, and the mixture was stirred at room temperature for 1 hr or more. After the reaction, water (100 mL) was added dropwise thereto at 30° C. or below to quench the reaction, and the ethyl acetate (200 mL) was added thereto. The organic layer was separated, and concentrated under reduced pressure to the volume of about 30 mL. To the residue was added diisopropyl ether (100 mL), and the mixture was concentrated to the volume of about 20 mL under reduced pressure. These operations were repeated twice to adjust the volume to about 20 mL. The crystals were collected by filtration, and washed with diisopropyl ether (20 mL), and then washed twice with water (50 mL). The obtained wet crystals were dried under reduced pressure at an outside temperature of 50° C. to give t-butyl 4-formyl-1H-imidazole-1-carboxylate (16.0 g, 81.5 mmol). yield 78%.

$^1$H NMR (500 MHz, DMSO-d$_6$) δ 1.60 (s, 9H), 8.37-8.39 (m, 2H), 9.81 (s, 1H).

Reference Example 5

6-(7-Hydroxy-6,7-dihydro-5H-pyrrolo[1,2-c]imidazol-7-yl)-N-methyl-2-naphthamide (5.20 kg, 16.9 mol), ethanol (130 L) and activated carbon (260 g) were stirred at room temperature, and the insoluble material was filtered off, and washed with ethanol (15.6 L). The above-mentioned operations were repeated three times. The filtrates and washings were combined, and (2S,3S)-tartranilic acid (15.95 kg, 70.8 mol) and ethanol (20.8 L) were added thereto. The mixture was heated to about 50° C., allowed to cool to room temperature, stirred for about 4 hr, cooled to about 0° C., and stirred for about 1 hr. The precipitated crystals were collected by filtration, and washed with ethanol (31.2 L). The obtained wet crystals (about 23 kg) in ethanol (156 L) were stirred at room temperature for about 2 hr, and the mixture was cooled to about 0° C., and stirred for about 1 hr. The precipitated crystals were collected by filtration, and washed with ethanol (31.2 L). The obtained wet crystals (about 20 kg) were added to 1 mol/L aqueous sodium hydroxide solution (104 L), and the mixture was stirred at room temperature for about 1 hr. The precipitated crystals were collected by filtration, washed with water (93.6 L), and dried under reduced pressure to a constant amount to give 6-(7S)-hydroxy-6,7-dihydro-5H-pyrrolo[1,2-c]imidazol-7-yl)-N-methyl-2-na-phthamide 1 hydrate (4.11 kg, 12.6 mol). yield 25%. containing 5.6 wt % water (by Karl-Fisher water measurement).

The powder X-ray diffraction pattern of 6-((7S)-hydroxy-6,7-dihydro-5H-pyrrolo[1,2-c]imidazol-7-yl)-N-methyl-2-naphthamide 1 hydrate is shown in FIG. 1.

Reference Example 6

6-(7S)-Hydroxy-6,7-dihydro-5H-pyrrolo[1,2-c]imidazol-7-yl)-N-methy-1-2-naphthamide 1 hydrate (4.05 kg, 12.4 mol) was added to 60% aqueous methanol solution (118 L), and dissolved with heating to about 70° C. Activated carbon (203 g) was added thereto at the same temperature, and the insoluble material was filtered off, and washed with 60% aqueous methanol solution (11.6 L). The filtrate and washing were combined, and heated to about 73° C. to dissolve the precipitated crystals, the solution was cooled to about 55° C., and water (25.9 L) was added thereto. While cooling, the mixture was stirred at room temperature for about 1 hr, and then at about 0° C. for about 2 hr. The precipitated crystals were collected by filtration, washed with 50% aqueous methanol solution (12.2 L), and dried under reduced pressure to a constant amount to give 6-(7S)-hydroxy-6,7-dihydro-5H-pyrrolo[1,2-c]imidazol-7-yl)-N-methyl-2-naphthamide anhydride (3.13 kg, 10.2 mol). yield 82%.

Figure 2:
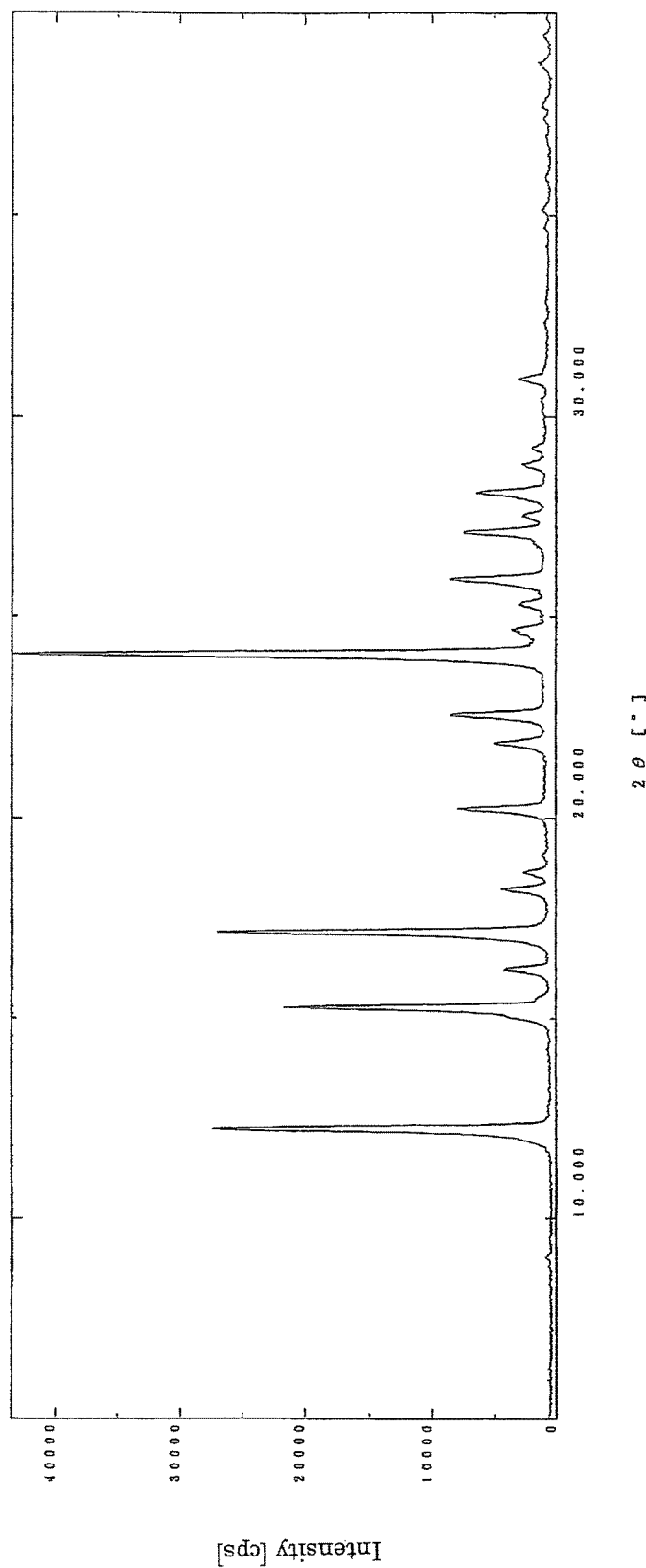
FIG. 2 shows a powder X-ray diffraction pattern of 6-((7S)-hydroxy-6,7-dihydro-5H-pyrrolo[1,2-c]imidazol-7-yl)-N-methyl-2-na-phthamide anhydride.

The powder X-ray diffraction pattern of 6-((7S)-hydroxy-6,7-dihydro-5H-pyrrolo[1,2-c]imidazol-7-yl)-N-methyl-2-naphthamide anhydride is shown in FIG. 2.

Reference Example 7

6-Bromo-2-naphthoic acid (10.1 g, 40.1 mmol) and N,N-dimethylformamide (4.75 g, 65.0 mmol) were added to toluene (80 mL). To the reaction mixture was added dropwise thionyl chloride (5.7 g, 48.2 mmol) at 45 to 50° C., and the mixture was stirred for 1 hr, and allowed to cool to room temperature. The reaction mixture was added dropwise at 10 to 25° C. to a solution prepared by adding triethylamine (11.4 g, 112.4 mmol) and 40% methylamine methanol solution (8.1 g, 104.4 mmol) to toluene (80 mL), and the mixture was stirred at room temperature for 1 hr. To the reaction mixture was added dropwise water (50 mL), and the mixture was stirred at room temperature. The crystals were collected by filtration, and washed with a mixed solvent (25 mL) of methanol/water (2:8) to give wet crystals. The total amount of the wet crystals was added to N,N-dimethylacetamide (70 mL), and dissolved with heating to 60° C. The reaction mixture was allowed to cool to room temperature, and water (140 mL) was added dropwise thereto. The crystals were collected by filtration, and washed with water (80 mL) to give wet crystals. The total amount of the wet crystals was suspended in ethyl acetate (25 mL) with stirring at room temperature. The crystals were collected by filtration, and washed with ethyl acetate (5 mL). The obtained wet crystals were dried under reduced pressure to give 6-bromo-N-methyl-2-naphthamide (9.4 g, 35.6 mmol). yield 89%.

$^1$H NMR (500 MHz, DMSO-d$_6$) δ 2.84 (d, J=4.4 Hz, 3H), 7.71 (dd, J=8.8, 2.2 Hz, 1H), 7.93-8.03 (m, 3H), 8.28 (d, J=1.9 Hz, 1H), 8.44 (s, 1H), 8.62 (d, J=4.1 Hz, 1H); HRMS (ESI) m/z Calcd for a $C_{12}H_{11}NOBr$ [M+H]$^+$: 264.0024. Found: 264.0019; Anal. Calcd for a $C_{12}H_{10}NOBr$: C, 54.57; H, 3.82; N, 5.30; Br, 30.25. Found: C, 54.56; H, 3.70; N, 5.34; Br, 30.23.

Reference Example 8

Under a nitrogen atmosphere, o-bromotrifluoromethylbenzene (1.35 kg, 6.00 mol) was added to tetrahydrofuran (7.9 L). The reaction mixture was cooled to −70° C., 1.6 mol/L n-butyllithium hexane solution (3.75 L, 6.00 mol) was added dropwise thereto, and the mixture was stirred at the same temperature for about 30 min. The reaction mixture was added dropwise at the same temperature to a solution prepared by adding 6-bromo-N-methyl-2-naphthamide (1.13 kg, 4.28 mol) to THF (62.2 L) at −70° C. under a nitrogen atmosphere, and the mixture was stirred for 1.5 hr.

To the reaction mixture were added dropwise successively 1.6 mol/L n-butyllithium hexane solution (2.67 L, 4.27 mol) and a solution of 1-trityl-4-formyl-1H-imidazole (1.21 kg, 3.58 mol) in THF (7.9 L) at the same temperature, and the mixture was stirred for 2 hr. The reaction mixture was allowed to warm to −10° C., and 20 w/v % aqueous ammonium chloride solution (17.0 L) was added dropwise thereto at −10 to 0° C. The separated organic layer was concentrated under reduced pressure. To the residue was added ethyl acetate (11.3 L), and the mixture was stirred at room temperature. The crystals were collected by filtration, and washed with ethyl acetate (11.3 L). The obtained wet crystals were dried under reduced pressure to give 6-[hydroxy(1-trityl-1H-imidazol-4-yl)methyl]-N-methyl-2-naphthamide (1.31 kg, 2.50 mol). yield 58%.

Reference Example 9

To glucosamine hydrochloride (200 g, 0.928 mol) were added water (300 mL) and ammonium thiocyanate (212 g, 2.78 mol, 3.0 equivalents) at 25° C., and the mixture was stirred at 80 to 89° C. for 8 hr. The reaction mixture was allowed to cool to 60° C., water (300 mL) and seed crystals were added thereto, and the mixture was stirred at 25 to 40° C. for 15 hr. The crystals were collected by filtration, washed twice with water (100 mL), and vacuum-dried (50° C.) to a constant amount to give (1R,2S,3R)-1-(2-sulfanyl-1H-imidazol-4-yl)butane-1,2,3,4-tetraol (101.4 g). yield 50%.

Reference Example 10

Under nitrogen stream, to (1R,2S,3R)-1-(2-sulfanyl-1H-imidazol-4-yl)butane-1,2,3,4-tetraol (10 g, 45.4 mmol) was added water (40 mL), and to the obtained suspension was added dropwise an aqueous diluted solution of 30% aqueous hydrogen peroxide (15.4 g, 136 mmol, 3.0 equivalents) in water (40 mL) over 10 min at 17 to 43° C. (the compound was gradually dissolved to give an uniform pale-yellow solution). The reaction mixture was stirred at 24 to 36° C. for 4 hr, and barium carbonate (27 g, 136 mmol, 3.0 equivalents) was added over 5 min at 24 to 26° C. (neutralized to pH 7), and the mixture was stirred at 25 to 26° C. for 1 hr and 20 min. The insoluble material was filtered off, and washed with water (40 mL). To the filtrate and washing was added sodium sulfite (11.4 g, 90.8 mmol, 2.0 equivalents) over 5 min at 20 to 32° C. The obtained aqueous solution was stirred at 26 to 32° C. for 1 hr and 30 min to give an aqueous solution of (1R,2S,3R)-1-(1H-imidazol-4-yl)butane-1,2,3,4-tetraol. To this aqueous solution was added sodium periodate (29.1 g, 136 mmol, 3.0 equivalents) over 10 min at 12 to 30° C., and the mixture was stirred at 27 to 30° C. for 1 hr and 30 min. To the reaction mixture was added sodium periodate (2.91 g, 13.6 mmol, 0.3 equivalents) at 27 to 30° C., and the mixture was stirred at 27 to 30° C. for 2 hr. The insoluble material was filtered off, and washed four times with water (10 mL). To the filtrate and washing was added methanol (500 mL), and the inorganic salt was filtered off, and washed twice with methanol (50 mL). To the filtrate and washing was added activated carbon (3 g, SHIRASAGI A, trade name), and the mixture was stirred at room temperature for 1 hr. The insoluble material was filtered off, and washed with methanol. The filtrate and washing were concentrated under reduced pressure to give a crude compound (9.37 g). To the crude compound were added water (3 mL) and seed crystals for crystallization, and the mixture was stirred at room temperature for 24 hr, and then for 2 hr under ice-cooling. The crystals were collected by filtration, washed with cooled water (1 mL), and vacuum-dried (50° C.) to a constant amount to give 4(5)-formylimidazole (2.35 g). yield 54%.

Reference Example 11

To 4(5)-formylimidazole (2 g, 20.8 mmol) were added DMAc (30 mL) and triethylamine (3.5 mL, 25.0 mmol, 1.2 equivalents), and then trityl chloride (4.06 g, 14.6 mmol, 0.7 equivalents) was added thereto at room temperature. The mixture was stirred at room temperature for 24 hr, and to the reaction mixture was added water (60 mL) at room temperature, and the mixture was stirred at room temperature for 2 hr. The crystals were collected by filtration, washed with water, and vacuum-dried (50° C.) to a constant amount to give a crude compound (4.6 g). To the crude compound (0.2 g) was added methanol (1 mL), and the mixture was stirred at room temperature for 2 hr. The crystals were collected by filtration, was washed with methanol (0.2 mL), and vacuum-dried (50° C.) to a constant amount to give 1-trityl-4-formyl-1H-imidazole (0.14 g). yield 65%.

Example 1

Under a nitrogen atmosphere, 6-bromo-N-methyl-2-naphthamide (7.0 g, 26.5 mmol) was added to tetrahydrofuran (175 mL), and then 2.0 mol/L isopropylmagnesium chloride tetrahydrofuran solution (13.7 mL) was added dropwise thereto at room temperature. The reaction mixture was cooled to −30° C., 1.6 mol/L n-butyllithium hexane solution (26.6 mL) was added dropwise thereto, and the mixture was stirred at the same temperature for 2 hr. To the reaction mixture was added dropwise a solution of 1-trityl-4-formyl-1H-imidazole (13.5 g, 39.9 mmol) in tetrahydrofuran (140 mL) at −20° C., and the mixture was stirred at the same temperature for 2 hr. The reaction mixture was allowed to warm to 0° C., and stirred for 1 hr, and 20 w/v % aqueous ammonium chloride solution (105 mL) was added dropwise thereto. The organic layer was separated, and concentrated to the volume of about 90 mL under reduced pressure. To the residue was added tetrahydrofuran (140 mL), and the mixture was concentrated to the volume of about 90 mL under reduced pressure. To the residue was added acetone (140 mL), and the mixture was concentrated to the volume of about 140 mL under reduced pressure. These operations were repeated three times. To the residue was added acetone to adjust the volume to about 180 mL, and the mixture was stirred at room temperature. The crystals were collected by filtration, and washed with acetone (70 mL). The obtained wet crystals were dried under reduced pressure to give 6-[hydroxy(1-trityl-1H-imidazol-4-yl)methyl]-N-methyl-2-naphthamide (10.3 g, 19.7 mmol). yield 74%.
$^1$H NMR (500 MHz, DMSO-$d_6$) δ 2.84 (d, J=4.7 Hz, 3H), 5.76 (d, J=5.0 Hz, 1H), 5.82 (d, J=4.7 Hz, 1H), 6.80 (s, 1H), 6.98-7.13 (m, 6H), 7.28 (d, J=1.6 Hz, 1H), 7.32-7.50 (m, 9H), 7.55 (dd, J=8.5, 1.6 Hz, 1H), 7.83-7.99 (m, 4H) 8.37 (s, 1H) 8.58 (d, J=4.4 Hz, 1H); HRMS (ESI) m/z Calcd for a $C_{35}H_{30}N_3O_2$[M+H] 524.2338. Found: 524.2325; Anal. Calcd for a $C_{35}H_{29}N_3O_2$: C, 80.28; H, 5.58; N, 8.02. Found: C, 80.17; H, 5.80; N, 7.81.

Example 2

Under a nitrogen atmosphere, 6-bromo-N-methyl-2-naphthamide (1.0 g, 3.79 mmol) was added to tetrahydrofuran (25 mL), and then 1.0 mol/L dibutylmagnesium heptane solution (2.0 mL) was added dropwise thereto at room temperature. The obtained solution was cooled to −13° C., 1.6 mol/L n-butyllithium hexane solution (2.6 mL) was added dropwise thereto, and the mixture was stirred at the same temperature for 1.5 hr. A solution of 1-trityl-4-formyl-1H-imidazole (1.4 g, 4.2 mmol) in tetrahydrofuran (15 mL) was added dropwise to the reaction mixture at −11° C., and the mixture was stirred at the same temperature for 5 hr. The reaction mixture was allowed to warm to 6° C. over 2.5 hr, and 20 w/v % aqueous ammonium chloride solution (30 mL) was added dropwise thereto. The organic layer was separated, and quantified to give 6-[hydroxy(1-trityl-1H-imidazol-4-yl)methyl]-N-methyl-2-naphthamide (1.2 g, 2.24 mmol). yield 71%.

Example 3

6-[Hydroxy(1-trityl-1H-imidazol-4-yl)methyl]-N-methyl-2-naphthamide (10.0 g, 19.1 mmol) and manganese dioxide (10.0 g, 115.0 mmol) were added to a mixed solvent of N,N-dimethylacetamide (25 mL) and ethyl acetate (63 mL), and the mixture was stirred at 60° C. for 3 hr. The insoluble material was filtered off at the same temperature, and washed with ethyl acetate (60 mL). The filtrate and washing were combined and concentrated to the volume of 30 mL under reduced pressure. To the residue was added dropwise diisopropyl ether (100 mL), and the mixture was stirred at room temperature. The obtained crystals were collected by filtration, and washed with diisopropyl ether (30 mL) to give crude wet crystals (26.4 g). The crude wet crystals (10.8 g) were added to ethyl acetate (54 mL), and the mixture was warmed to 60° C., and stirred for 0.5 hr. The obtained mixture was allowed to cool to room temperature, and diisopropyl ether (108 mL) was added dropwise thereto. The mixture was stirred with cooling to 5° C. The obtained crystals were collected by filtration, and washed with a mixed solvent (27 mL) of diisopropyl ether/ethyl acetate (2:1, volume ratio). The obtained wet crystals were dried under reduced pressure to give N-methyl-6-[(1-trityl-1H-imidazol-4-yl)carbonyl]-2-naphthamide (8.2 g, 15.7 mmol). yield 82%.
$^1$H NMR (500 MHz, DMSO-$d_6$) δ 2.85 (d, J=4.7 Hz, 3H), 7.17-7.22 (m, 6H), 7.40-7.50 (m, 9H), 7.69 (d, J=1.4 Hz, 1H), 7.77 (d, J=1.4 Hz, 1H), 7.99 (dd, J=8.5, 1.6 Hz, 1H), 8.13 (dd, J=18.4, 8.7 Hz, 2H), 8.21 (dd, J=8.5, 1.6 Hz, 1H), 8.48 (s, 1H), 8.68 (q, J=4.4 Hz, 1H), 9.01 (s, 1H); HRMS (ESI) m/z Calcd for a $C_{35}H_{28}N_3O_2$[M+H] 522.2182. Found: 522.2177; Anal. Calcd for a $C_{35}H_{27}N_3O_2$: C, 80.59; H, 5.22; N, 8.06. Found: C, 80.51; H, 5.17, N, 8.10.

Example 4

6-[Hydroxy(1-trityl-1H-imidazol-4-yl)methyl]-N-methyl-2-naphthamide (10.0 g, 19.1 mmol) and manganese dioxide (6.6 g, 75.9 mmol) were added to N,N-dimethylacetamide (85 mL), and the mixture was stirred at 60° C. for 2 hr. The insoluble material was filtered off at the same temperature, and washed with N,N-dimethylacetamide (40 mL). The filtrate and washing were combined and cooled to 40° C., water (60 mL) was added dropwise thereto, and the mixture was stirred at room temperature. The obtained crystals were collected by filtration, and washed with water (50 mL). The wet crystals were dried under reduced pressure to give crude crystals (9.5 g). Ethyl acetate (100 mL) was warmed to 40° C., and the crude crystals (9.5 g) were added thereto. The obtained mixture was warmed to 50° C., and stirred for 0.5 hr. The solvent (20 mL) was evaporated under reduced pressure. The residue was allowed to cool to room temperature, and diisopropyl ether (80 mL) was added dropwise thereto, and the mixture was stirred at the same temperature. The obtained crystals were collected by filtration, and washed with a mixed solvent (30 mL) of diisopropyl ether/ethyl acetate (1:1, volume ratio). The obtained wet crystals were dried under reduced pressure to give N-methyl-6-[(1-trityl-1H-imidazol-4-yl)carbonyl]-2-naphthamide (8.9 g, 17.1 mmol). yield 89%.

Example 5

Under a nitrogen atmosphere, 6-[hydroxy(1-trityl-1H-imidazol-4-yl)methyl]-N-methyl-2-naphthamide (1.0 g, 1.91 mmol) was added to N,N-dimethylacetamide (50 mL), and then sodium hydride (oil, 0.15 g, 3.85 mmol) was added at room temperature, and the mixture was stirred at the same temperature for about 60 hr. To the reaction mixture were added dropwise water (50 mL) and 1 mol/L hydrochloric acid (5 mL) at room temperature, and the mixture was stirred at the same temperature for 45 min. Then, the reaction mixture was cooled to 0° C., and stirred for 2 hr. The crystals were collected by filtration, and washed with water (30 mL). The obtained wet crystals were dried under reduced pressure to give N-methyl-6-[(1-trityl-1H-imidazol-4-yl)carbonyl]-2-naphthamide (0.89 g, 1.71 mmol). yield 90%.

Example 6

Under a nitrogen atmosphere, zinc powder (15.0 g, 229.4 mmol) was suspended in tetrahydrofuran (57 mL), trimethylsilyl chloride (1.5 mL, 11.5 mmol) was added thereto at room temperature, and the mixture was stirred for 30 min. The reaction mixture was heated to 40° C., a solution of ethyl bromoacetate (12.7 mL, 114.5 mmol) in tetrahydrofuran (144 mL) was added dropwise thereto, and the mixture was stirred at the same temperature for 30 min. The reaction mixture was kept stand at room temperature, the excess amount of zinc was filtered off to give a reaction mixture containing (bromo(2-ethoxy-2-oxoethyl)zinc (hereinafter to be abbreviated as Reformatsky reagent). The prepared Reformatsky reagent (89.6 mL, corresponding to 2.5 eq.) was cooled to 0° C., cinchonine (7.1 g, 24.0 mmol), pyridine (6.2 mL, 76.8 mmol) and tetrahydrofuran (80 mL) were added thereto, and the mixture was stirred at the same temperature for 30 min. The reaction mixture was cooled to −25° C., N-methyl-6-[(1-trityl-1H-imidazol-4-yl)carbonyl]-2-naphthamide (10.0 g, 19.2 mmol) and tetrahydrofuran (20 mL) were added thereto, and the mixture was stirred at the same temperature for 1 hr and 45 min. The Reformatsky reagent (35.7 mL, corresponding to 1.0 eq.) was added thereto at the same temperature, and the mixture was stirred for 1 hr. To the reaction mixture were added ethyl acetate (140 mL) and 20 w/v % aqueous citric acid solution (140 mL) at 10° C. or below. The organic layer was separated, and washed with 10% sodium chloride-containing 20 w/v % aqueous citric acid solution (100 mL) at 5° C. (twice), 5 w/v % aqueous sodium bicarbonate (100 mL) (three times), and water (100 mL). The organic layer was concentrated to the volume of 60 mL under reduced pressure. To the residue was added methanol (100 mL), and the mixture was concentrated to the volume of 60 mL under reduced pressure. To the residue was added methanol to adjust the volume to 200 mL. Water (20 mL) was added thereto at room temperature, and the mixture was stirred for 1 hr. Then water (140 mL) was added dropwise thereto at the same temperature, and the mixture was stirred. The obtained crystals were collected by filtration, and washed with a mixed solvent (60 mL) of methanol/water (1:3, volume ratio). The obtained wet crystals were dried under reduced pressure to give ethyl(3S)-3-hydroxy-3-{6-[(methylamino)carbonyl]-2-naphthyl}-3-(1-trityl-1H-im-idazol-4-yl)propanoate (11.3 g, 18.5 mmol). yield: 97%. enantiomeric excess: 96% ee.

$^1$H NMR (500 MHz, DMSO-d$_6$) δ 0.93 (t, J=7.1 Hz, 3H), 2.84 (d, J=4.4 Hz, 3H), 3.20 (d, J=14.2 Hz, 1H), 3.29 (d, J=14.5 Hz, 1H), 3.86 (t, J=6.9 Hz, 2H), 5.86 (s, 1H), 6.79 (d, J=1.6 Hz, 1H), 7.06 (dd, J=7.9, 1.9 Hz, 6H), 7.31 (d, J=1.3 Hz, 1H), 7.33-7.45 (m, 9H), 7.73 (dd, J=8.7, 1.7 Hz, 1H), 7.82-7.95 (m, 3H), 8.02 (s, 1H), 8.36 (s, 1H), 8.58 (q, J=4.7 Hz, 1H); HRMS (ESI) m/z Calcd for a $C_{39}H_{36}N_3O_4$ [M+H]$^+$: 610.2706. Found: 610.2698; Anal. Calcd for a $C_{39}H_{36}N_3O_4$: C, 76.83; H, 5.79; N, 6.89. Found: C, 76.79; H, 5.95; N, 6.81.

Example 7

To a solution of anhydrous calcium chloride (4.55 g, 41.0 mmol) in ethanol (62.5 mL) was added sodium borohydride (3.11 g, 82.0 mmol) at −7° C., and the mixture was stirred at −7° C. for 30 min. To the reaction mixture were added dropwise a solution of ethyl(3S)-3-hydroxy-3-{6-[(methylamino)carbonyl]-2-naphthyl}-3-(1-trityl-1H-im-idazol-4-yl)propanoate (10.0 g, 16.4 mmol) in tetrahydrofuran (80 mL), and tetrahydrofuran (20 mL) at −5° C. The reaction mixture was stirred at 5° C. for 8 hr, water (80 mL), 1 mol/L hydrochloric acid (82 mL) and ethyl acetate (200 mL) were added dropwise thereto at 5° C., and the mixture was stirred. To the separated organic layer was added 0.2 mol/L hydrochloric acid (82 mL) at 5° C., and the mixture was stirred, and adjusted to pH 7.5 with 0.5 mol/L aqueous sodium hydroxide solution at the same temperature. To the separated organic layer was added again 0.2 mol/L hydrochloric acid (82 mL) at 5° C., and the mixture was stirred, and adjusted to pH 7.5 with 0.5 mol/L aqueous sodium hydroxide solution at the same temperature. To the separated organic layer was added water (100 mL), and the mixture was adjusted to pH 9.5 with 0.5 mol/L aqueous sodium hydroxide solution. The separated organic layer was washed with 10 w/v % brine (100 mL). To the separated organic layer was added water (120 mL), and the mixture was stirred with heating to 60° C. for 4 hr. The separated organic layer was concentrated to the volume of about 38 mL at the same temperature under reduced pressure. To the residue was added ethyl acetate (80 mL), and the mixture was concentrated to the volume of about 38 mL under reduced pressure. These operations were repeated three times. To the residue was added ethyl acetate to adjust the volume to about 38 mL. Diisopropyl ether (75 mL) was added thereto, and the mixture was stirred with cooling to 5.degree. C. The crystals were collected by filtration, and washed with a mixed solvent (30 mL) of diisopropyl ether/ethyl acetate (2:1, volume ratio). The obtained wet crystals were dried under reduced pressure to give 6-[(1S)-1,3-dihydroxy-1-(1-trityl-1H-imidazol-4-yl)propyl]-N-methyl-2-naphthamide (8.7 g, 15.3 mmol). yield 94%. enantiomeric excess: 94% ee.

$^1$H NMR (500 MHz, DMSO-d$_6$) δ 2.19-2.35 (m, 1H), 2.40-2.49 (m, 1H), 2.83 (d, J=4.7 Hz, 3H), 3.38 (ddd, J=19.2, 8.8, 5.4 Hz, 2H), 4.47 (t, J=5.0 Hz, 1H), 5.7 (s, 1H), 6.9 (d, J=1.6 Hz, 1H), 7.00-7.12 (m, 6H), 7.32 (d, J=1.6 Hz, 1H), 7.34-7.45 (m, 9H) 7.75 (dd, J=8.7, 1.7 Hz, 1H), 7.82-7.97 (m, 3H), 8.00 (s, 1H), 8.36 (s, 1H), 8.6 (q, J=4.3 Hz, 1H); HRMS (ESI) m/z Calcd for a $C_{37}H_{34}N_3O_3$[M+H] 568.2600. Found: 568.2590.

Example 8

To THF (100 mL) and water (63 μg, 3.5 mmol) was added 6-[(1S)-1,3-dihydroxy-1-(1-trityl-1H-imidazol-4-yl)propyl]-N-methyl-2-nap-hthamide (10.0 g, 17.6 mmol). The reaction mixture was cooled to 10° C., and ethyldiisopropylamine (3.41 g, 26.4 mmol) and methanesulfonyl chloride (3.03 g, 26.4 mmol) were successively added thereto, and the mixture was stirred at room temperature for 1 hr. To the reaction mixture was added a solution of sodium carbonate (3.73 g, 35.2 mmol) in water (40 mL), and the mixture was warmed to 57° C., and stirred for 5 hr. The mixture was concentrated under reduced pressure to adjust the volume of the residue to 45 mL. Ethyl acetate (50 mL) was added thereto at 45° C., and the mixture was stirred. The reaction mixture was stirred with cooling to room temperature and then cooling to 5° C. The crystals were collected by filtration, and washed with ethyl acetate (40 mL) cooled to 5° C. The obtained wet crystals were dried under reduced pressure to give crude 6-((7S)-hydroxy-6,7-dihydro-5H-pyrrolo[1,2-c]imidazol-7-yl)-N-methyl-2-na-phthamide (5.3 g, 17.3 mmol). yield 98%.

Example 9

The crude 6-((7S)-hydroxy-6,7-dihydro-5H-pyrrolo[1,2-c]imidazol-7-yl)-N-methyl-2-naphthamide obtained in Example 8 (5.0 g, 16.3 mmol) was added to methanol (97.5 mL) and purified water (38 mL), and dissolved with heating to 70° C., and activated carbon (0.25 g) was added thereto. The reaction mixture was stirred at the same temperature for 20 min, and the activated carbon was filtered off, and washed with 72% methanol (5 mL). The filtrate and washing were combined, and purified water (35.5 mL) was added dropwise thereto at 55 to 60° C. The reaction mixture was stirred with cooling to 30° C., purified water (35.5 mL) was added thereto at the same temperature, and the mixture was stirred. The reaction mixture was stirred with cooling to 2° C., and the crystals were collected by filtration, and washed with 45% methanol (15 mL). The obtained wet crystals were dried under reduced pressure to give 6-((7S)-hydroxy-6,7-dihydro-5H-pyrrolo[1,2-c]imidazol-7-yl)-N-methyl-2-naphthamide (4.17 g, 13.6 mmol). yield 83%. enantiomeric excess: 99% ee.

$^1$H NMR (500 MHz, DMSO-$d_6$) δ 2.84 (m, 1H), 2.88 (d, J=4.4 Hz, 3H), 2.93 (m, 1H), 4.19 (m, 1H), 4.25 (m, 1H), 6.26 (s, 1H), 6.69 (s, 1H), 7.65 (m, 1H), 7.66 (s, 1H), 7.95 (dd, J=8.5, 1.6 Hz, 1H), 8.00 (d, J=8.5 Hz, 2H), 8.09 (brs, 1H), 8.45 (brs, 1H), 8.65 (q, J=4.4 Hz, 1H); MS (EI) m/z 307 [M]+; Anal. Calcd for a $C_{18}H_{17}N_3O_2$: C, 70.34; H, 5.58; N, 13.67. Found: C, 70.31; H, 5.50; N, 13.66.

Example 10

To a mixture of toluene (100 mL), THF (20 mL) and 1 mol/L hydrochloric acid (100 mL) was added 6-[(1S)-1,3-dihydroxy-1-(1-trityl-1H-imidazol-4-yl)propyl]-N-methyl-2-naphthamide (10.0 g, 17.6 mmol). The reaction mixture was stirred vigorously at 60° C. for 2 hr. The reaction mixture was allowed to cool to room temperature. The aqueous layer was separated, and the obtained aqueous layer was washed twice with methyl tert-butyl ether (100 mL and 50 mL). To the obtained aqueous layer was added methanol (10 mL), and then carbonate (10.6 g) and water (10 mL) were added thereto. The obtained slurry was stirred overnight at room temperature. The obtained crystals were collected by filtration, and washed with 10% aqueous methanol. The obtained wet crystals were dried under reduced pressure to give crude crystals (5.56 g). To a mixture of methanol (30 mL) and water (3 mL) were added the crude crystals (4 g). After stirring at 50° C. for 1 hr, water (50 mL) was added to the slurry at 50° C. over 1 hr. The slurry was stirred at 50° C. for 1 hr, and then allowed to cool to room temperature. After stirring for 3 hr at room temperature, the crystals were collected by filtration and washed with water. The obtained wet crystals were dried under reduced pressure to give 6-[(1S)-1,3-dihydroxy-1-(1H-imidazol-4-yl)propyl]-N-methyl-2-naphthamide (3.69 g, 11.3 mmol). yield 89%.

$^1$H NMR (500 MHz, DMSO-$d_6$) δ 2.33-2.39 (m, 1H), 2.47-2.52 (m, 1H), 2.83 and 2.79 (d, J=4.4 Hz, total 3H), 3.33 (br s, 1H), 3.47 (br s, 1H), 4.54 and 4.59 (br s, total 1H), 5.58 and 5.97 (s, total 1H), 6.83 and 6.94 (s, total 1H), 7.47 and 7.58 (s, total 1H), 7.53 and 7.75 (d, J=8.5 Hz, total 1H), 7.83-7.99 (m, 3H), 8.03 and 8.06 (s, 1H), 8.36 and 8.38 (s, 1H), 8.57 (d, J=4.1 Hz, 1H), 11.75 and 11.83 (s, total 1H); Anal. Calcd for $C_{18}H_{19}N_3O_3$: C, 66.45; H, 5.89; N, 12.91; O, 14.75. Found: C, 66.19; H, 5.99; N, 12.72.

Example 11

To a solution of 6-[(1S)-1,3-dihydroxy-1-(1H-imidazol-4-yl)propyl]-N-methyl-2-naphthamide (1.0 g, 3.1 mmol) in tetrahydrofuran (100 mL) were added N-ethyldiisopropylamine (2.39 g, 18.4 mmol) and methanesulfonyl chloride (2.11 g, 18.4 mmol) at room temperature. The mixture was stirred at the same temperature for 3 hr. To the reaction mixture was added a solution of sodium carbonate (1.31 g, 12.3 mmol) in water (3 mL). The mixture was heated to 60° C. and stirred for 5 hr. After the reaction mixture was allowed to cool to room temperature, ethyl acetate (25 mL) was added thereto. The organic layer was separated and concentrated under reduced pressure. Methanol (16.7 mL) and water (6.4 mL) were added to the residue. The mixture was heated to 65° C., and activated carbon (45 mg) was added thereto. After stirring at the same temperature for 30 min, the activated carbon was filtered off and washed with methanol (1.1 mL). Water (6.4 mL) was added to the filtrate at 55° C. The resulting mixture was allowed to cool to room temperature and stirred for 30 min. To the mixture was added water (6.4 mL) at the same temperature, and the mixture was stirred for 2 hr. The mixture was cooled to 0° C. and stirred for 2 hr. The obtained precipitated crystals were collected by filtration, washed with 45% aqueous methanol (3 mL), and dried under reduced pressure to give 6-((7S)-hydroxy-6,7-dihydro-5H-pyrrolo[1,2-c]imidazol-7-yl)-N-methyl-2-naphthamide (540 mg, 1.8 mmol). yield 57%.

Example 12

Under a nitrogen atmosphere, 6-bromo-N-methyl-2-naphthamide (10.0 g, 38 mmol) was added to tetrahydrofuran (250 mL), and then 2.0 mol/L isopropylmagnesium chloride tetrahydrofuran solution (19 mL) was added dropwise thereto at room temperature. The obtained reaction mixture was cooled to −20° C., 1.6 mol/L n-butyllithium hexane solution (40 mL) was added dropwise to the reaction mixture, and the mixture was stirred at the same temperature for 2 hr. To the obtained reaction mixture was added dropwise a solution of 1-N,N-dimethylaminosulfonyl-4-formyl-1H-imidazole (11.6 g, 57 mmol) in tetrahydrofuran (200 mL) at −20° C., and the mixture was stirred at the same temperature for 2 hr. The obtained reaction mixture was allowed to warm to 0° C., and stirred for 1 hr, and 20 w/v % aqueous ammonium chloride solution (150 mL) was added dropwise to the reaction mixture. The reaction mixture was separated to the organic layer and aqueous layer, and the obtained organic layer was concentrated to the volume of about 90 mL under reduced pressure. To the obtained residue was added tetrahydrofuran (140 mL), and the obtained reaction mixture was concentrated to the volume of about 80 mL under reduced pressure. To the obtained residue was added ethyl acetate (250 mL), and the mixture was concentrated to the volume of about 80 mL under reduced pressure. These operations were repeated three times. To the obtained residue was added ethyl acetate to adjust the volume to about 200 mL to give a ethyl acetate solution containing 6-[hydroxy(1-N,N-dimethylaminosulfonyl-1H-imidazol-4-yl) methyl]-N-methyl-2-naphthamide.

The NMR data of the obtained 6-[hydroxy(1-N,N-dimethylaminosulfonyl-1H-imidazol-4-yl)methyl]-N-methyl-2-naphthamide was shown below.

$^1$H NMR (500 MHz, DMSO-$d_6$) δ 2.76-2.88 (m, 9H), 5.82 (s, 1H), 6.08 (s, 1H), 7.37-7.43 (m, 1H), 7.61 (dd, J=8.5, 1.58 Hz, 1H), 7.84-8.02 (m, 4H), 8.07 (d, J=1.3 Hz, 1H), 8.39 (s, 1H), 8.59 (d, J=4.1 Hz, 1H); HRMS (ESI) m/z Calcd for a $C_{18}H_{21}N_4O_4S[m+H]^+$: 389.1205. Found: 389.1273.

Example 13

To the ethyl acetate solution containing 6-[hydroxy(1-N,N-dimethylaminosulfonyl-1H-imidazol-4-yl)methyl]-N-methyl-2-naphthamide, which is obtained in Example 10, were added manganese dioxide (20.6 g, 237.2 mmol) and ethyl acetate (200 mL), and the mixture was stirred at 60° C. for 10 hr. The insoluble material was filtered off from the reaction mixture at the same temperature, and washed with ethyl acetate (200 mL). The filtrate and washing were combined, and concentrated under reduced pressure to adjust the volume to about 300 mL. Water (150 mL) was added thereto, and the organic layer was separated. These operations were repeated twice. The organic layers were combined, and stirred at room temperature about for 1 hr. To the reaction mixture was added dropwise diisopropyl ether (150 mL), and the mixture was stirred at room temperature for 2 hr to give crystals. The obtained crystals were collected by filtration, and washed with a mixed solvent (90 mL) of diisopropyl ether/ethyl acetate (2:1, volume ratio) to give wet crystals. The obtained wet crystals were dried under reduced pressure to give N-methyl-6-[(1-N,N-dimethylaminosulfonyl-1H-imidazol-4-yl)carbony-l]-2-naphthamide (8.9 g, 22.9 mmol). total yield from 6-bromo-N-methyl-2-naphthamide: 60%.

$^1$H NMR (500 MHz, DMSO-$d_6$) δ 2.84-2.91 (m, 3H), 2.93 (s, 6H), 8.02 (d, J=8.5 Hz, 1H), 8.14-8.23 (m, 3H), 8.43 (s, 1H), 8.47 (s, 1H), 8.51 (s, 1H), 8.71 (d, J=4.4 Hz, 1H), 8.94 (s, 1H); HRMS (ESI) m/z Calcd for a $C_{18}H_{19}N_4O_4S$ $[m+H]^+$: 387.1049. Found: 387.1118.

Example 14

Under a nitrogen atmosphere, zinc powder (15.0 g, 229.4 mmol) was suspended in tetrahydrofuran (57 mL), trimethylsilyl chloride (1.5 mL, 11.5 mmol) was added thereto at room temperature, and the mixture was stirred for 30 min. The reaction mixture was heated to 40° C., and to the reaction mixture was added dropwise a solution of ethyl bromoacetate (12.7 mL, 114.5 mmol) in tetrahydrofuran (144 mL). The obtained reaction mixture was stirred at 30 min for 40° C., and kept stand at room temperature, and the excess amount of zinc was filtered off to give a reaction mixture containing bromo(2-ethoxy-2-oxoethyl)zinc (hereinafter to be abbreviated as Reformatsky reagent). The obtained Reformatsky reagent (49.7 mL, corresponding to 2.5 eq.) was cooled to 0° C. or below, and to the Reformatsky reagent were added cinchonine (3.8 g, 12.9 mmol), pyridine (3.4 mL, 41.4 mmol) and tetrahydrofuran (32 mL). The obtained reaction mixture was stirred for 15 min, and cooled to −20° C., and to the reaction mixture were added N-methyl-6-[(1-N,N-dimethylaminosulfonyl-1H-imidazol-4-yl)carbonyl]-2-naphthamide (4.0 g, 10.4 mmol) and tetrahydrofuran (12 mL). The obtained reaction mixture was stirred at −20° C. for 1 hr. To the obtained reaction mixture was added the Reformatsky reagent (25.0 mL, corresponding to 1.25 eq.) at −20° C., the obtained reaction mixture was stirred for 30 min. To the obtained reaction mixture were added ethyl acetate (100 mL) and 20 w/v % aqueous citric acid solution (100 mL) at 10° C. or below. The separated organic layer was washed with 10% sodium chloride-containing 20 w/v % aqueous citric acid solution (100 mL) at 5° C. (twice), 5 w/v % aqueous sodium bicarbonate (100 mL) (three times), and the water (100 mL). The organic layer was concentrated to the volume of 20 mL under reduced pressure to give a residue. To the obtained residue was added methanol (50 mL), and the mixture was concentrated to the volume of 20 mL under reduced pressure to give a residue. These operations were repeated again. To the obtained residue was added water (8 mL), and the obtained solution was stirred for 1 hr. To the reaction mixture was added dropwise water (32 mL), and the mixture was stirred to give crystals. The obtained crystals were collected by filtration, and washed with a mixed solvent (30 mL) of methanol/water (1:3, volume ratio) to give wet crystals. The obtained wet crystals were dried under reduced pressure to give ethyl (3S)-3-hydroxy-3-{6-[(methylamino)carbonyl]-2-naphthyl}-3-(1-N,N-dimethyl-aminosulfonyl-1H-imidazol-4-yl) propanoate (4.29 g, 9.04 mmol). yield 87%. enantiomeric excess: 85% ee.

$^1$H NMR (500 MHz, DMSO-$d_6$) δ 0.94 (t, J=7.1 Hz, 3H), 2.78 (s, 6H), 2.84 (d, J=4.7 Hz, 3H), 3.21-3.31 (m, 1H), 3.31-3.42 (m, 1H), 3.80-3.95 (m, 2H), 6.12 (s, 1H), 7.38 (d, J=1.6 Hz, 1H), 7.75 (dd, J=8.7, 1.73 Hz, 1H), 7.85-7.99 (m, 3H), 8.06-8.14 (m, 2H), 8.38 (s, 1H), 8.58 (d, J=4.4 Hz, 1H); HRMS (ESI) m/z Calcd for a $C_{22}H_{27}N_4O_6S[m+H]^+$: 475.1573. Found: 475.1635.

Example 15

To a solution of anhydrous calcium chloride (2.05 g, 18.5 mmol) in ethanol (26.5 mL) was added sodium borohydride (1.40 g, 36.9 mmol) at −17° C., and the mixture was stirred at −16-−7° C. for 30 min. To the obtained reaction mixture was added dropwise a solution of ethyl(3S)-3-hydroxy-3-{6-[(methylamino)carbonyl]-2-naphthyl}-3-(1-N,N-dimethyl-aminosulfonyl-1H-imidazol-4-yl)propanoate (3.5 g, 7.38 mmol) in tetrahydrofuran (36 mL) at −20° C. The obtained reaction mixture was stirred for 6 hr at 0° C., to the reaction mixture were added dropwise water (36 mL), 1 mol/L hydrochloric acid (37 mL) and ethyl acetate (90 mL) at 5° C., and the mixture was stirred. To the separated organic layer was added 0.2 mol/L hydrochloric acid (37 mL) at 5° C., and the mixture was stirred, and adjusted about pH 7.5 with 0.5 mol/L aqueous sodium hydroxide solution at 5° C. To the separated organic layer was added again 0.2 mol/L hydrochloric acid (37 mL) at 5° C., and the mixture was stirred, and adjusted to about pH 7.5 with 0.5 mol/L aqueous sodium hydroxide solution at the same temperature. To the separated organic layer was added water (45 mL), and the mixture was adjusted to about pH 9.5 with 0.5 mol/L aqueous sodium hydroxide solution. The separated organic layer was washed with 10 w/v % brine (45 mL). To the separated organic layer was added water (54 mL), and the mixture was heated to 60° C., and stirred for 4 hr. The separated organic layer was completely concentrated under reduced pressure to give 6-[1S)-1,3-dihydroxy-1-(1-N,N-dimethylaminosulfonyl-1H-imidazol-4-yl)pro-pyl]-N-methyl-2-naphthamide (2.1 g, 4.83 mmol). yield 66%. enantiomeric excess: 86% ee.

$^1$H NMR (500 MHz, DMSO-$d_6$) δ 2.34-2.47 (m, 1H), 2.78 (s, 6H), 2.82-2.86 (m, 3H), 3.35-3.48 (m, 2H), 4.50 (t, J=4.9 Hz, 1H), 5.92 (s, 1H), 7.36 (d, J=1.3 Hz, 1H), 7.76 (dd, J=8.7, 1.73 Hz, 1H), 7.87-7.98 (m, 3H), 8.06-8.14 (m, 2H), 8.37 (s, 1H), 8.57 (q, J=4.3 Hz, 1H); HRMS (ESI) m/z Calcd for a $C_{20}H_{25}N_4O_5S[m+H]^+$: 433.1467. Found: 433.1535.

Example 16

Under a nitrogen atmosphere, 6-bromo-N-methyl-2-naphthamide (10.0 g, 37.9 mmol) was added to tetrahydrofuran (250 mL), and to the obtained solution was added dropwise 2.0 mol/L isopropylmagnesium chloride tetrahydrofuran solution (18.9 mL) at room temperature. The obtained reaction mixture was cooled to −30° C., 1.65 mol/L n-butyllithium hexane solution (37.9 mL) was added dropwise thereto, and the mixture was stirred at the same temperature for 1 hr or more. To the obtained reaction mixture was added dropwise a solution of 1-tosyl-4-formyl-1H-imidazole (14.2 g, 56.8 mmol) in tetrahydrofuran (200 mL) at −20° C., and the mixture was stirred at the same temperature for 2 hr. The obtained reaction mixture was warmed over 2 hr to 0° C., 20 w/v % aqueous ammonium chloride solution (150 mL) was added dropwise thereto. The separated organic layer was concentrated to the volume of about 130 mL under reduced pressure to give a residue. To the obtained residue was added tetrahydrofuran (200 mL), and the mixture was concentrated to the volume of about 130 mL under reduced pressure to give a residue. To the obtained residue was added acetone (200 mL), and the mixture was concentrated to the volume of about 200 mL under reduced pressure. These operations were repeated three times to give a residue. To the obtained residue was added acetone to adjust the volume to about 260 mL. The obtained solution was stirred at room temperature for 2 hr or more. The obtained crystals were collected by filtration, and washed with acetone (100 mL) to give wet crystals. The obtained wet crystals were dried under reduced pressure at an outside temperature of 50° C. to give 6-(hydroxy(1-tosyl-1H-imidazol-4-yl)methyl)-N-methyl-2-naphthamide (8.5 g, 19.5 mmol). yield 52%.

$^1$H NMR (500 MHz, DMSO-$d_6$) δ 2.40 (s, 3H), 2.83 (d, J=5.0 Hz, 1H), 5.74 (d, J=5.0 Hz, 1H), 6.05 (d, J=5.0 Hz, 1H), 7.49-7.51 (m, 3H), 7.55-7.56 (m, 1H), 7.88-7.92 (m, 4H), 7.98-7.99 (m, 2H), 8.27 (s, 1H), 8.37 (s, 1H), 8.58-8.59 (q, J=5.0 Hz, 1H); HRMS (ESI) m/z Calcd for a $C_{23}H_{22}N_3O_4S[m+H]$ 436.1286. Found: 436.1322.

Example 17

6-(Hydroxy(1-tosyl-1H-imidazol-4-yl)methyl)-N-methyl-2-naphthamide (8.2 g, 18.8 mmol) and manganese dioxide (14.7 g, 169.1 mmol) were added to N,N-dimethylacetamide (70 mL), and the mixture was stirred at 60° C. for 7 hr. The insoluble material was filtered off from the obtained reaction mixture at 60° C., and washed with N,N-dimethylacetamide (33 mL). The filtrate and washing were combined, and cooled to 40° C., water (49 mL) was added dropwise thereto, and the mixture was stirred at the same temperature for 0.5 hr or more, and then at room temperature for 1 hr or more to give crystals. The obtained crystals were collected by filtration, and washed with water (51 mL) to give wet crystals. The obtained wet crystals were dried under reduced pressure at an outside temperature of 50° C. to give crude crystals (6.6 g). Ethyl acetate (66 mL) were warmed to 40° C., and the crude crystals (6.6 g) were added thereto. The obtained mixture was warmed to 50° C., and stirred for 0.5 hr or more, and 13 mL of the solvent was evaporated under reduced pressure. The obtained residue was allowed to cool to room temperature, diisopropyl ether (53 mL) was added dropwise thereto at the same temperature, and the mixture was stirred to give crystals. The obtained crystals were collected by filtration, and washed with a mixed solvent (20 mL) of diisopropyl ether/ethyl acetate (1:1, volume ratio) to give wet crystals. The obtained wet crystals were dried under reduced pressure at an outside temperature of 50° C. to give N-methyl-6-[(1-tosyl-1H-imidazol-4-yl)carbonyl]-2-naphthamide (6.5 g, 15.0 mmol). yield 79%.

$^1$H NMR (500 MHz, DMSO-$d_6$) δ 2.42 (s, 3H), 2.85 (d, J=5.0 Hz, 3H), 7.55-7.56 (m, 2H), 8.01-8.02 (m, 1H), 8.12-8.17 (m, 5H), 8.49 (s, 1H), 8.61-8.64 (d, J=15.0 Hz, 2H), 8.69 (q, 1H), 8.86 (s, 1H); HRMS (ESI) m/z Calcd for a $C_{23}H_{20}N_3O_4S[m+H]^+$: 434.1130. Found: 434.1168.

Example 18

The Reformatsky reagent was obtained according to the method described in Example 14. The obtained Reformatsky reagent (27.1 mL, corresponding to 2.5 eq.) was cooled to 0° C., cinchonine (2.1 g, 7.2 mmol) and pyridine (1.9 mL, 23.0 mmol) was added thereto, and the mixture was stirred at the same temperature for 30 min. The reaction mixture was cooled to −25° C., N-methyl-6-[(1-tosyl-1H-imidazol-4-yl)carbonyl]-2-naphthamide (2.5 g, 5.76 mmol) was added thereto, and the mixture was stirred at the same temperature for 1 hr. To the obtained reaction mixture was added the Reformatsky reagent (10.9 mL, corresponding to 1.0 eq.) at −25° C., and the mixture was stirred for 1 hr. The Reformatsky reagent (5.4 mL, corresponding to 0.5 eq.) was added again −25° C., and the mixture was stirred for 1 hr. To the obtained reaction mixture were added ethyl acetate (35 mL) and 20 w/v % aqueous citric acid solution (35 mL) at 10° C. or below. The separated organic layer was washed with 10% sodium chloride-containing 20 w/v % aqueous citric acid solution (35 mL) at 5.degree. C. (twice), 5 w/v % aqueous sodium bicarbonate (35 mL) (three times), and water (35 mL). The separated organic layer was concentrated under reduced pressure to give ethyl(3S)-3-hydroxy-3-{6-[(methylamino)carbonyl]-2-naphthyl}-3-(1-tosyl-1H-imi-dazol-4-yl)propanoate (2.92 g, 5.6 mmol). yield: 97%.

$^1$H NMR (500 MHz, DMSO-$d_6$) δ 0.79 (t, J=7.1 Hz, 3H), 2.39 (s, 3H), 2.83 (d, J=4.7 Hz, 3H), 3.19 (d, J=14.2 Hz, 1H), 3.30 (d, J=14.2 Hz, 1H), 3.76 (t, J=6.9 Hz, 2H), 6.13 (s, 1H), 7.44-7.52 (m, 3H), 7.68 (dd, J=8.7, 2.1 Hz, 1H), 7.85-7.94 (m, 3H), 7.97 (d, J=8.2 Hz, 2H), 8.00-8.03 (m, 1H), 8.26-8.41 (m, 2H), 8.57 (d, J=4.7 Hz, 1H).

Example 19

To a solution of anhydrous calcium chloride (1.86 g, 16.3 mmol) in ethanol (32 mL) were added sodium borohydride (1.27 g, 33.6 mmol) and ethanol (5 mL) at −10° C., and the mixture was stirred at −10° C. for 30 min. To the reaction mixture were added dropwise a solution of ethyl (3S)-3-hydroxy-3-{6-[(methylamino)carbonyl]-2-naphthyl}-3-(1-tosyl-1H-imi-dazol-4-yl)propanoate (2.5 g, 5.6 mmol) in tetrahydrofuran (73 mL)/ethanol (10 mL), and tetrahydrofuran (5 mL) at −10° C. The obtained reaction mixture was stirred at 5° C. for 6 hr, and to the obtained reaction mixture were added dropwise water (100 mL), 1 mol/L hydrochloric acid (40 mL) and ethyl acetate (200 mL) at 10° C. or below, and the mixture was stirred. To the separated organic layer was added 0.2 mol/L hydrochloric acid (14 mL) at 5° C., and the mixture was stirred. The reaction mixture was adjusted to pH 7.5 with 0.5 mol/L aqueous sodium hydroxide solution at 5° C. To the separated organic layer was added again 0.2 mol/L hydrochloric acid (14 mL) at 5° C., and the mixture was stirred. The reaction mixture was adjusted to pH 7.5 with 0.5 mol/L aqueous sodium hydroxide solution at 5° C. To the separated organic layer was added water (10 mL), and the mixture was adjusted to pH 9.5 with 0.5 mol/L aqueous sodium hydroxide solution. To the separated organic layer was added water (120 mL), and the mixture was heated to 60° C., and stirred for 3 hr. The separated organic layer was concentrated at 60° C. under reduced pressure to give 6-[(1S)-1,3-dihydroxy-1-(1-tosyl-1H-imidazol-4-yl)propyl]-N-methyl-2-naphthamide (2.9 g, 6.1 mmol).

$^1$H NMR (500 MHz, DMSO-d$_6$) δ 2.36-2.47 (m, 1H), 2.38 (d, J=2.5 Hz, 3H), 2.59-2.71 (m, 1H), 2.83 (d, J=4.7 Hz, 3H), 3.61-3.68 (m, 1H), 3.68-3.76 (m, 1H), 4.45-4.47 (m, 1H), 5.91 (s, 1H), 7.42-7.45 (m, 1H), 7.45-7.51 (m, 2H), 7.68 (dt, J=8.7, 2.1 Hz, 1H), 7.72 (s, 1H), 7.84-7.93 (m, 2H), 7.93-8.03 (m, 4H), 8.27-8.40 (m, 2H), 8.48-8.65 (m, 1H).

Example 20

To a solution of anhydrous calcium chloride (1.86 g, 16.3 mmol) in ethanol (32 mL) were added sodium borohydride (1.27 g, 33.6 mmol) and ethanol (5 mL) at −10° C., and the mixture was stirred at −10° C. for 30 min. To the reaction mixture was added dropwise a solution of ethyl(3S)-3-hydroxy-3-{6-[(methylamino)carbonyl]-2-naphthyl}-3-(1-tosyl-1H-imi-dazol-4-yl)propanoate (2.5 g, 5.6 mmol) in tetrahydrofuran (73 mL)/ethanol (10 mL), and tetrahydrofuran (5 mL) at −10° C. The obtained reaction mixture was stirred at 7° C. for 21 hr, and to the obtained reaction mixture were added dropwise water (100 mL), 1 mol/L hydrochloric acid (40 mL) and ethyl acetate (200 mL) at 10° C. or below, and the mixture was stirred. To the separated organic layer was added 0.2 mol/L hydrochloric acid (14 mL) at 5° C., and the mixture was stirred. The reaction mixture was adjusted to pH 7.5 with 0.5 mol/L aqueous sodium hydroxide solution at 5° C. To the separated organic layer was added again 0.2 mol/L hydrochloric acid (14 mL) at 5° C., and the mixture was stirred. The reaction mixture was adjusted to pH 7.5 with 0.5 mol/L aqueous sodium hydroxide solution at 5° C. To the separated organic layer was added water (10 mL), and the mixture was adjusted to pH 9.5 with 0.5 mol/L aqueous sodium hydroxide solution. To the separated organic layer was added water (120 mL), and the mixture was heated to 60° C., and stirred for 3 hr. The separated organic layer was concentrated at 60° C. under reduced pressure to give 6-[(1S)-1,3-dihydroxy-1-(1H-imidazol-4-yl)propyl]-N-methyl-2-naphthamide (2.3 g, 7.0 mmol).

Example 21

To THF (4.8 mL) was added 6-[(1S)-1,3-dihydroxy-1-(1-tosyl-1H-imidazol-4-yl)propyl]-N-methyl-2-naphthamide (479.6 mg, 1.0 mmol). The reaction mixture was cooled to 10° C., and ethyldiisopropylamine (505.9 mg, 4.0 mmol) and methanesulfonyl chloride (458.8 mg, 4.0 mmol) were successively added thereto, and the mixture was stirred at room temperature for 2 hr. To the reaction mixture was added a solution of sodium carbonate (530.0 mg, 5.0 mmol) in water (2 mL), and the mixture was warmed to 57° C., and stirred for 5 hr. The separated organic layer was concentrated under reduced pressure. Methanol (4 mL) and activated carbon (40 mg) were added thereto. The reaction mixture was stirred at the same temperature for 20 min, and the activated carbon was filtered off, and washed with methanol (2 mL). The filtrate and washing were concentrated under reduced pressure. Methanol (1 mL), ethyl acetate (5 mL), and THF (10 mL) were added to the residue, and the mixture was washed twice with 10% sodium chloride-containing 5 w/v % aqueous sodium bicarbonate solution (15 mL). The separated organic layer was concentrated under reduced pressure to give 6-(7S)-hydroxy-6,7-dihydro-5H-pyrrolo[1,2-c]imidazol-7-yl)-N-methyl-2-naphthamide (135.4 mg, 0.44 mmol). yield 44%.

Example 22

Under a nitrogen atmosphere, 6-bromo-N-methyl-2-naphthamide (10.0 g, 37.9 mmol) was added to tetrahydrofuran (250 mL), and to the obtained solution was added dropwise 2.0 mol/L isopropylmagnesium chloride tetrahydrofuran solution (18.9 mL) at room temperature. The obtained reaction mixture was cooled to −30° C., 1.65 mol/L n-butyllithium hexane solution (37.9 mL) was added dropwise thereto, and the mixture was stirred at the same temperature for 1 hr or more. To the reaction mixture was added dropwise a solution of 1-(phenylsulfonyl)-4-formyl-1H-imidazole (13.4 g, 56.8 mmol) in tetrahydrofuran (100 mL) at −20° C., and the mixture was stirred at the same temperature for 2 hr. The reaction mixture was warmed over 2 hr to 0° C., and 20 w/v % aqueous ammonium chloride solution (150 mL) was added dropwise thereto. The separated organic layer was concentrated to the volume of about 130 mL under reduced pressure to give a residue. To the obtained residue was added tetrahydrofuran (200 mL), and the mixture was concentrated to the volume of about 130 mL under reduced pressure to give a residue. To the obtained residue was added ethyl acetate (200 mL), and the mixture was concentrated to the volume of about 200 mL under reduced pressure. These operations were repeated three times to give a residue. To the obtained residue was added ethyl acetate to adjust the volume to about 200 mL. The obtained reaction mixture was stirred at room temperature for 2 hr or more to give crystals. The crystals was collected by filtration, and washed with ethyl acetate (100 mL) to give wet crystals. The obtained wet crystals were dried under reduced pressure at an outside temperature of 50° C. to give 6-(hydroxy(1-(phenylsulfonyl)-1H-imidazol-4-yl)methyl)-N-methyl-2-naphthamide (9.2 g, 21.8 mmol). yield 58%.

$^1$H NMR (500 MHz, DMSO-d$_6$) δ 2.83 (d, J=5.0 Hz, 3H), 5.74 (d, J=5.0 Hz, 1H), 6.06 (d, J=5.0 Hz, 1H), 7.69-7.72 (m, 2H), 7.81-7.84 (m, 1H), 7.90-7.94 (m, 4H), 8.11-8.13 (m, 2H), 8.30 (s, 1H), 8.37 (s, 1H), 8.57-8.59 (q, 1H).

Example 23

6-(Hydroxy(1-(phenylsulfonyl)-1H-imidazol-4-yl)methyl)-N-methyl-2-naphthamide (8.8 g, 20.88 mmol) and manganese dioxide (16.4 g, 187.9 mmol) were added to N,N-dimethylacetamide (75 mL), and the mixture was stirred at 60° C. for 9.5 hr. The insoluble material was filtered off from the reaction mixture at 60° C., and washed with DMAc (35 mL). The filtrate and washing were combined, and cooled to 40° C., water (53 mL) was added dropwise thereto, and the mixture was stirred at the same temperature for 0.5 hr or more, and then at room temperature for 1 hr or more to give crystals. The obtained crystals were collected by filtration, and washed with water (44 mL) to give wet crystals. The obtained wet crystals were dried under reduced pressure at an outside temperature of 50° C. to give crude crystals (6.3 g). Ethyl acetate (63 mL) was warmed to 40° C., and the crude crystals (6.3 g) were added thereto. The obtained mixture was warmed to 50° C., and stirred for 0.5 hr or more. 13 mL of the solvent was evaporated under reduced pressure to give a residue. The obtained residue was allowed to cool to room temperature, diisopropyl ether (53 mL) was added dropwise thereto at the same temperature, and the mixture was stirred to give crystals. The obtained crystals were collected by filtration, and washed with a mixed solvent (20 mL) of diisopropyl ether/ethyl acetate (1:1, volume ratio) to give wet crystals. The obtained wet crystals were dried under reduced pressure at an outside temperature of 50° C. to give N-methyl-6-[(1-(phenylsulfonyl)-1H-imidazol-4-yl)carbonyl]-2-naphthamide (6.2 g, 14.9 mmol). yield 72%.

$^1$H NMR (500 MHz, DMSO-d$_6$) δ 2.86 (d, J=5.0 Hz, 3H), 7.76 (t, J=10.0 Hz, 2H), 7.88 (t, J=10.0 Hz, 1H), 8.00 (d, J=10.0 Hz, 1H), 8.12 (q, J=5.0 Hz, 2H), 8.18 (d, J=10.0 Hz, 1H), 8.27 (d, J=10.0 Hz, 2H), 8.49 (s, 1H), 8.67 (d, J=10.0 Hz, 2H), 8.71 (q, J=5.0 Hz, 1H), 8.86 (s, 1H).

Example 24

The Reformatsky reagent was obtained according to the method described in Example 14. The obtained Reformatsky reagent (27.3 mL, corresponding to 2.5 eq.) was cooled to 0° C. or below, cinchonine (2.6 g, 8.9 mmol), pyridine (2.3 mL, 23.0 mmol) and THF (24 mL) were added thereto, and the mixture was stirred at the same temperature for 30 min. The reaction mixture was cooled to −25° C., N-methyl-6-((1-phenylsulfonyl-1H-imidazol-4-yl)carbonyl)-2-naphthamide (3.0 g, 7.2 mmol) was added thereto. The obtained reaction mixture was stirred at −20° C. for 1 hr. To the obtained reaction mixture was added the Reformatsky reagent (10.9 mL, corresponding to 1.0 eq.) at −25° C., and the mixture was stirred for 1.5 hr. The Reformatsky reagent (10.9 mL, corresponding to 1.0 eq.) was added again thereto −25° C., and the mixture was stirred for 1.5 hr. To the obtained reaction mixture were added ethyl acetate (42 mL) and 20 w/v % aqueous citric acid solution (42 mL) at 10° C. or below. The separated organic layer was washed successively with 10% sodium chloride-containing 20 w/v % aqueous citric acid solution (30 mL, twice) at 5° C., 5 w/v % aqueous sodium bicarbonate (30 mL, three times), and water (30 mL). The organic layer was concentrated to the volume of 18 mL under reduced pressure to give a residue. To the obtained residue was added methanol (30 mL), and the mixture was concentrated to the volume of 18 mL under reduced pressure to give a residue. To the residue was added methanol to adjust the volume to 30 mL. Water (3 mL) was added thereto at room temperature, and the mixture was stirred for 1 hr. Then water (21 mL) was added dropwise thereto at the same temperature, and the mixture was stirred. The obtained crystals were collected by filtration, and washed with a mixed solvent (9 mL) of methanol/water (1:3, volume ratio). The obtained wet crystals were dried under reduced pressure to give ethyl(3S)-3-hydroxy-3-{6-[(methylamino)carbonyl]-2-naphthyl}-3-(1-phenylsulfon-yl-1H-imidazol-4-yl)propanoate (3.2 g, 6.3 mmol). yield 88%. enantiomeric excess: 61% ee.

$^1$H NMR (500 MHz, DMSO-d$_6$) δ 0.78 (t, J=5.0 Hz, 3H), 2.82 (d, J=5.0 Hz, 3H), 3.19 (d, J=15.0 Hz, 1H), 3.30 (d, J=15.0 Hz, 1H), 3.76 (q, J=5.0 Hz, 2H), 6.15 (s, 1H), 7.50 (d, J=5.0 Hz, 1H), 7.69 (dd, J=15.0, 10.0 Hz, 3H), 7.79 (t, J=/010.0 Hz, 1H), 7.87-7.92 (m, 3H), 8.02 (s, 1H), 8.09-8.12 (m, 2H), 8.34 (s, 1H), 8.58 (q, J=5.0 Hz, 1H).

Example 25

To a solution of anhydrous calcium chloride (0.84 g, 7.4 mmol) in ethanol (9 mL) was added sodium borohydride (0.57 g, 14.8 mmol) at −15° C., and the mixture was stirred at −10° C. for 30 min. To the reaction mixture was added dropwise a solution of ethyl(3S)-3-hydroxy-3-{6-[(methylamino)carbonyl]-2-naphthyl}-3-(1-phenylsulfon-yl-1H-imidazol-4-yl)propanoate (1.5 g, 3.0 mmol) in tetrahydrofuran (75 mL)/ethanol (15 mL) at −10° C. The obtained reaction mixture was stirred at 5° C. for 8 hr, and to the obtained reaction mixture were added dropwise water (12 mL), 1 mol/L hydrochloric acid (15 mL) and ethyl acetate (30 mL) at 10° C. or below, and the mixture was stirred. To the separated organic layer was added 0.2 mol/L hydrochloric acid (15 mL) at 5° C., and the mixture was stirred. The reaction mixture was adjusted to pH 7.5 with 0.5 mol/L aqueous sodium hydroxide solution at 5° C. To the separated organic layer was added again 0.2 mol/L hydrochloric acid (15 mL) at 5° C., and the mixture was stirred. The reaction mixture was adjusted to pH 7.5 with 0.5 mol/L aqueous sodium hydroxide solution at 5° C. To the separated organic layer was added water (15 mL), and the mixture was adjusted to pH 9.5 with 0.5 mol/L aqueous sodium hydroxide solution. The separated organic layer was washed with 10 w/v % brine (15 mL). To the separated organic layer was added water (18 mL), and the mixture was heated to 60° C., and stirred for 3 hr. The separated organic layer was concentrated under reduced pressure to give 6-[(1S)-1,3-dihydroxy-1-(1-phenylsulfonyl-1H-imidazol-4-yl)propyl]-N-meth-yl-2-naphthamide (1.2 g, 2.5 mmol). yield 83%. enantiomeric excess: 62% ee.

$^1$H NMR (500 MHz, DMSO-d$_6$) δ 2.13-2.17 (m, 1H), 2.34-2.42 (m, 1H), 2.83 (d, J=5.0 Hz, 3H), 3.52-3.54 (m, 2H), 4.49 (t, J=5.0 Hz, 1H), 5.38 (s, 1H), 7.28-7.33 (m, 2H), 7.48 (d, J=5.0 Hz, 1H), 7.70 (dd, J=10.0, 5.0 Hz, 3H), 7.80 (t, J=10.0 Hz, 1H), 7.95-8.01 (m, 3H), 8.04-8.12 (m, 1H), 8.34 (s, 1H), 8.45 (s, 1H), 8.62 (q, J=5.0 Hz, 1H); HRMS (ESI) m/z calcd for $C_{24}H_{24}N_3O_5S$ [m+H]$^+$: 466.1392. Found: 466.1436.

Example 26

Under a nitrogen atmosphere, 6-bromo-N-methyl-2-naphthamide (5.0 g, 18.9 mmol) was added to tetrahydrofuran (125 mL), and to the obtained solution was added dropwise 2.0 mol/L isopropylmagnesium chloride tetrahydrofuran solution (9.5 mL) at room temperature. The obtained reaction mixture was cooled to −30° C., 1.65 mol/L n-butyllithium hexane solution (18.9 mL) was added dropwise thereto, and the mixture was stirred at the same temperature for 1 hr or more. To the reaction mixture was added dropwise a solution of t-butyl 4-formyl-1H-imidazole-1-carboxylate (6.7 g, 34.1 mmol) in tetrahydrofuran (50 mL) at −20° C., and the mixture was stirred at the same temperature for 2 hr. The obtained reaction mixture was warmed over 2 hr to 0° C., and 20 w/v % aqueous ammonium chloride solution (75 mL) was added dropwise thereto. The separated organic layer was concentrated to the volume of about 65 mL under reduced pressure to give a residue. To the obtained residue was added tetrahydrofuran (100 mL), and the mixture was concentrated to the volume of about 65 mL under reduced pressure to give a residue. To the obtained residue was added acetone (100 mL), and the mixture was concentrated to the volume of about 100 mL under reduced pressure. These operations were repeated three times to give a residue. The obtained residue was concentrated to dryness to give t-butyl 4-(hydroxy(6-methylcarbamoyl)naphthalen-2-yl)methyl)-1H-imidazole-1-carboxylate (10.5 g). HRMS (ESI) m/z Calcd for a $C_{21}H_{24}N_3O_4$ [m+H]$^+$; 382.1722. Found: 382.1759.

Example 27 t-Butyl 4-(hydroxy(6-methylcarbamoyl)naphthalen-2-yl)methyl)-1H-imidazole-1-carboxylate (10.2 g) and manganese dioxide (15.0 g, 172.5 mmol) were added to N,N-dimethylacetamide (35 mL), and the mixture was stirred at 60° C. for 14 hr. The insoluble material was filtered off from the obtained reaction mixture at 60° C., and washed with N,N-dimethylacetamide (25 mL). The filtrate and washing were combined, and concentrated under reduced pressure, and to the obtained residue were added ethyl acetate (100 mL) and water (50 mL). The separated organic layer was concentrated under reduced pressure to give t-butyl 4-(6-(methylcarbamoyl)-2-naphthoyl)-1H-imidazole-1-carboxylate (11.4 g).

HRMS (ESI) m/z calcd for a $C_{21}H_{24}N_3O_4$ [M+H]$^+$; 380.1566. Found: 380.1607.

INDUSTRIAL APPLICABILITY

According to the production method of the present invention, imidazole derivatives useful for the prophylaxis or treatment of diseases, for which androgen or estrogen is an aggravating factor, can be produced efficiently and industrially under mild conditions.

This application is based on patent application No. 2011-133712 filed in Japan, the contents of which are encompassed in full herein.

The invention claimed is:
1. A method of producing 6-(7-hydroxy-6,7-dihydro-5H-pyrrolo[1,2-c]imidazol-7-yl)-N-methyl-2-naphthamide or a salt thereof, which comprises:
reacting a compound represented by formula (I):

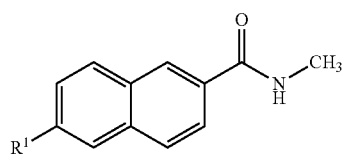
(I)

wherein $R^1$ is an iodine atom or a bromine atom,
with a compound represented by formula (II):

$R^2$—MgX (II)

wherein $R^2$ is a $C_{1-6}$ alkyl group or a $C_{6-12}$ aryl group; and
X is a chlorine atom, a bromine atom or an iodine atom,
or a compound represented by formula (III):

$R^2R^{2'}$—Mg (III)

wherein $R^{2'}$ is a $C_{1-6}$ alkyl group or a $C_{6-12}$ aryl group; and
$R^2$ is as defined above, then reacting the resulting compound with a compound represented by formula (IV):

$R^3$—Li (IV)

wherein $R^3$ is a $C_{1-6}$ alkyl group or a $C_{6-12}$ aryl group, and then reacting the resulting compound with a compound represented by formula (V):

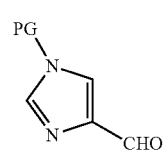
(V)

wherein PG is a protecting group,
or a salt thereof, thereby obtaining
a compound represented by formula (VI):

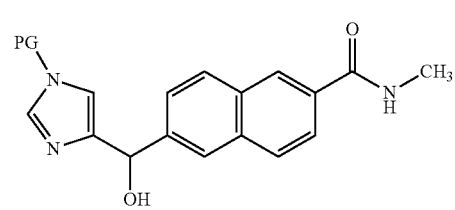
(VI)

wherein PG is as defined above,
or a salt thereof;
subjecting the compound represented by the formula (VI) to oxidation, thereby obtaining
compound represented by formula (VII):

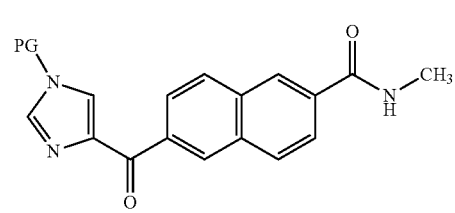
(VII)

wherein PG is as defined above,
or a salt thereof;
reacting the compound represented by the formula (VII) with a compound represented by formula (VIII):

BrZnCH$_2$CO$_2$—R$^4$ (VIII)

wherein $R^4$ is a $C_{1-6}$ alkyl group, thereby obtaining
a compound represented by formula (IX):

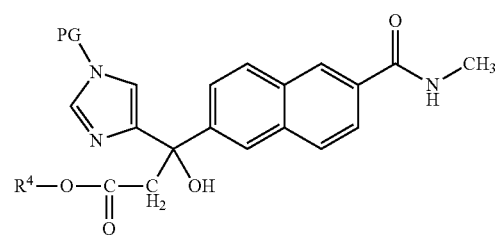
(IX)

wherein each symbol is as defined above,
or a salt thereof;
subjecting the compound represented by the formula (IX)
to reduction, thereby obtaining
a compound represented by formula (X):

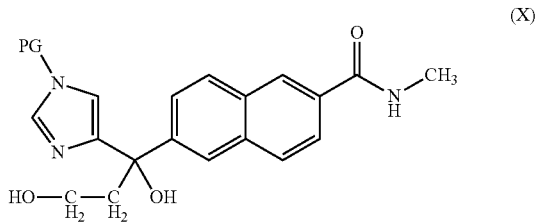

(X)

wherein PG is as defined above,
or a salt thereof; and
subjecting the compound reprensented by the formula (X)
to cyclization and deprotection.

2. A method of producing of 6-(7-hydroxy-6,7-dihydro-5H-pyrrolo[1,2-c]imidazol-7-yl)-N-methyl-2-naphthamide or a salt thereof, which comprises:
reacting a compound represented by the formula (VII):

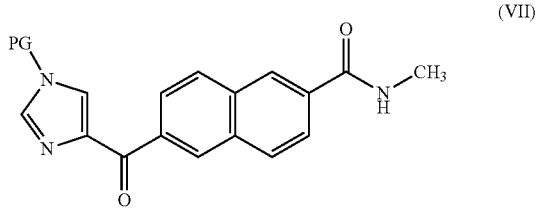

(VII)

wherein PG is a protecting group,
or a salt thereof, with a compound represented by the formula (VIII):

$$BrZnCH_2CO_2-R^4 \quad (VIII)$$

wherein $R^4$ is a $C_{1-6}$ alkyl group,
and then adding citric acid to the obtained reaction mixture, thereby obtaining
a compound represented by formula (IX):

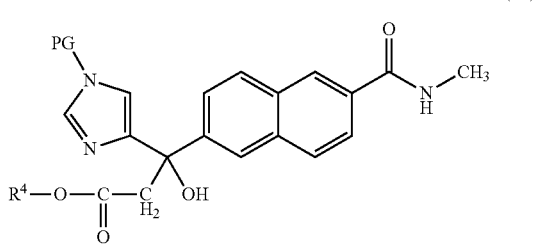

(IX)

wherein each symbol is as defined above,
or a salt thereof;
subjecting the compound represented by the formula (IX)
to reduction, thereby obtaining
a compound represented by formula (X):

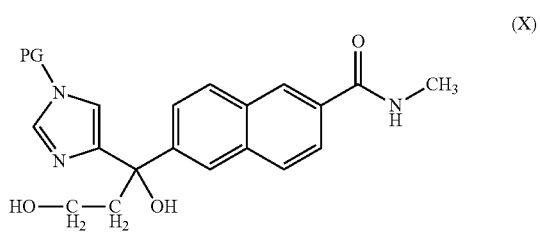

(X)

wherein PG is as defined above,
or a salt thereof; and
subjecting the compound represented by the formula (X)
to cyclization and deprotection.

3. The method of claim 1, wherein PG is trityl.

4. The method of claim 1, wherein PG is tosyl, benzenesulfonyl or N,N-dimethylaminosulfonyl.

5. The method of claim 1, wherein the reaction of the compound represented by the formula (VII) or a salt thereof with the compound represented by the formula (VIII) is reacting a compound represented by the formula:

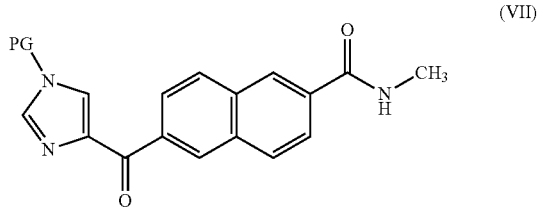

(VII)

wherein PG is a protecting group,
or a salt thereof, with a compound represented by the formula:

$$BrZnCH_2CO_2-R^4 \quad (VIII)$$

wherein $R^4$ is a $C_{1-6}$ alkyl group, and then adding citric acid to the obtained reaction mixture.

6. The method of claim 2, wherein PG is trityl.

7. The method of claim 2, wherein PG is tosyl, benzenesulfonyl or N,N-dimethylaminosulfonyl.

* * * * *